United States Patent
Cruz et al.

(10) Patent No.: US 10,000,595 B1
(45) Date of Patent: Jun. 19, 2018

(54) CATALYST SYSTEMS CONTAINING LOW VALENT TITANIUM COMPOUNDS AND POLYMERS PRODUCED THEREFROM

(71) Applicant: Chevron Phillips Chemical Company LP, The Woodlands, TX (US)

(72) Inventors: Carlos A. Cruz, Bartlesville, OK (US); Jared L. Barr, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days. days.

(21) Appl. No.: 15/481,502

(22) Filed: Apr. 7, 2017

(51) Int. Cl.
| | |
|---|---|
| C08F 4/642 | (2006.01) |
| C08F 110/02 | (2006.01) |
| C08F 210/16 | (2006.01) |
| C07F 7/28 | (2006.01) |
| C07F 9/535 | (2006.01) |

(52) U.S. Cl.
CPC .............. *C08F 210/16* (2013.01); *C07F 7/28* (2013.01); *C07F 9/5355* (2013.01); *C08F 4/642* (2013.01); *C08F 110/02* (2013.01); *C08F 2410/03* (2013.01)

(58) Field of Classification Search
CPC .......... C07F 7/28; C08F 4/642; C08F 110/02; C08F 210/16
See application file for complete search history.

(56) References Cited

U.S. PATENT DOCUMENTS

| | | |
|---|---|---|
| 3,242,099 A | 3/1966 | Manyik et al. |
| 3,248,179 A | 4/1966 | Norwood |
| 4,501,885 A | 2/1985 | Sherk et al. |
| 4,588,790 A | 5/1986 | Jenkins et al. |
| 4,794,096 A | 12/1988 | Ewen |
| 4,808,561 A | 2/1989 | Welborn, Jr. |
| 5,352,749 A | 10/1994 | Dechellis et al. |
| 5,436,304 A | 7/1995 | Griffin et al. |
| 5,565,175 A | 10/1996 | Hottovy et al. |
| 5,575,979 A | 11/1996 | Hanson |
| 5,576,259 A | 11/1996 | Hasegawa et al. |
| 5,739,220 A | 4/1998 | Shamshoum et al. |
| 5,807,938 A | 9/1998 | Kaneko et al. |
| 5,919,983 A | 7/1999 | Rosen et al. |
| 6,107,230 A | 8/2000 | McDaniel et al. |
| 6,165,929 A | 12/2000 | McDaniel et al. |
| 6,239,235 B1 | 5/2001 | Hottovy et al. |
| 6,262,191 B1 | 7/2001 | Hottovy et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,372,864 B1 | 4/2002 | Brown |
| 6,376,415 B1 | 4/2002 | McDaniel et al. |
| 6,388,017 B1 | 5/2002 | McDaniel et al. |

(Continued)

OTHER PUBLICATIONS

Alhomaidan et al., entitled "Hafnium-Phosphinimide Complexes," published in Can. J. Chem 87, 2009, pp. 1163-1172.

(Continued)

*Primary Examiner* — Caixia Lu
(74) *Attorney, Agent, or Firm* — Merchant & Gould P.C.

(57) ABSTRACT

Disclosed herein are methods for synthesizing low valence, bimetallic titanium compounds from half-metallocene titanium compounds and alkylaluminum compounds. The bimetallic titanium compounds can be used as components in catalyst systems for the polymerization of olefins.

20 Claims, 11 Drawing Sheets

(56) References Cited

U.S. PATENT DOCUMENTS

| | | | |
|---|---|---|---|
| 6,391,816 B1 | 5/2002 | McDaniel et al. |
| 6,395,666 B1 | 5/2002 | McDaniel et al. |
| 6,440,890 B1 | 8/2002 | Von Haken Spence et al. |
| 6,524,987 B1 | 2/2003 | Collins et al. |
| 6,548,441 B1 | 4/2003 | McDaniel et al. |
| 6,548,442 B1 | 4/2003 | Collins et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,777,509 B2 | 8/2004 | Brown et al. |
| 6,833,415 B2 | 12/2004 | Kendrick et al. |
| 6,984,695 B2 | 1/2006 | Brown et al. |
| 7,026,494 B1 | 4/2006 | Yang et al. |
| 7,041,617 B2 | 5/2006 | Jensen et al. |
| 7,199,073 B2 | 4/2007 | Martin et al. |
| 7,226,886 B2 | 6/2007 | Jayaratne et al. |
| 7,294,599 B2 | 11/2007 | Jensen et al. |
| 7,312,283 B2 | 12/2007 | Martin et al. |
| 7,517,939 B2 | 4/2009 | Yang et al. |
| 7,531,606 B2 | 5/2009 | Hendrickson |
| 7,534,842 B2 | 5/2009 | Jayaratne et al. |
| 7,598,327 B2 | 10/2009 | Conley et al. |
| 7,601,665 B2 | 10/2009 | McDaniel et al. |
| 7,619,047 B2 | 11/2009 | Yang et al. |
| 7,650,930 B2 | 1/2010 | Cheluget et al. |
| 7,884,163 B2 | 2/2011 | McDaniel et al. |
| 8,114,946 B2 | 2/2012 | Yang et al. |
| 8,309,485 B2 | 11/2012 | Yang et al. |
| 8,431,096 B2 | 4/2013 | Cheluget et al. |
| 8,431,657 B2 | 4/2013 | Wang et al. |
| 8,623,973 B1 | 1/2014 | McDaniel et al. |
| 8,703,886 B1 | 4/2014 | Yang et al. |
| 8,822,608 B1 | 9/2014 | Bhandarkar et al. |
| 9,023,959 B2 | 5/2015 | McDaniel et al. |
| 2004/0059070 A1 | 3/2004 | Whitte et al. |

OTHER PUBLICATIONS

Alhomaidan et al., entitled "Main Group Heterocycles from Lithiated Phosphinimines," published in Organometallics 2007, 26, pp. 3041-3048.

Alhomaidan et al., entitled Titanium Complexes of Amidophosphinimide Ligands†, published in Dalton Trans., 2009, pp. 1991-1998.

Alhomaidan et al., entitled "Use of Olefin Metathesis to Link Phosphinimide-Cyclopentadienyl Ligand Complexes: Synthesis, Structure, and Ethylene Polymerization Activity," published in Organometallics 2008, 27, pp. 6343-6352.

Beddie et al., entitled "Titanium Pyridyl-Phosphinimide Complexes—Synthesis, Structure, and Ethylene Polymerization Catalysis," published in Can J. Chem 84, 2006, pp. 755-761.

Beddie et al., entitled "Use of Computational and Synthetic Chemistry in Catalyst Design: A New Family of High-Activity Ethylene Polymerization Catalysts Based on Titanium Tris(amino)phosphinimide Complexes," published in Organometallics 2004, 23, pp. 5240-5251.

Cabrera et al., entitled "Cationic Methyl- and Chlorotitanium Phosphinimide Complexes," published in Organometallics 2005, 24, pp. 1091-1098.

Camacho-Bunquin et al., entitled "Hydrocarbon-Soluble Nanocatalysts with No Bulk Phase: Coplanar, Two-Coordinate Arrays of the Base Metals," published in J. Am. Chem. 2013, 135, pp. 5537-5540.

Carraz et al., entitled "Titanium Complexes of Sterically Demanding Cage-Phosphinimide Ligands," published in Organometallics 2000, 19, pp. 3791-3796.

Cornelissen et al., entitled "Chemistry of Metal—Metal-Bonded Early—Late Heterobimetallics: Cooperative Reactions of Functional Groups at a Persistent Organometallic Zr—Rh Framework," published in Organometallics 2005, 24, pp. 214-225.

Courtenay et al., entitled "Boron and Aluminum Complexes of Sterically Demanding Phosphinimines and Phosphinimides," published in Inorg. Chem. 2007, 46, pp. 3623-3631.

Courtenay et al., entitled "Phosphinimido Complexes of Silicon, Tin, and Germanium," published in Organometallics 2003, 22, pp. 818-825.

Courtenay et al., entitled "Synthesis and Reactivity of Neutral, Zwitterionic and Pentamethylcyclopentadienyl-Tantalum-Phosphinimide Complexes," published in Organometallics 2001, 20, pp. 1442-1450.

Courtenay et al., entitled "The Syntheses and Structures of Lithium Phosphinimide and Phosphinimine Complexes," published in Can. J. Chem 81, 2003, pp. 1471-1476.

Dehnicke et al., entitled "Phosphorane Iminato Complexes of Main Group Elements," published in Coordination Chemistry Reviews 158, 1997, pp. 103-169.

Friesen et al., entitled Selective Catalytic Dimerization of Neohexene by $[Cp*Ti(NP'Bu_3)Me][B(C_6F_5)_4]$, published in Organometallics 2008, 27, pp. 6596-6604.

Ghesner et al., entitled "Di-tert-butylbiphenylphosphinimide Titanium and Zirconium Complexes: Pendant Arene-Metal Interactions," published in Organometallics 2006, 25, pp. 4985-4995.

Graham et al., entitled "Reduction of Titanium(IV)-Phosphinimide Complexes: Routes to Ti(III) Dimers, Ti(IV)-Metallacycles, and Ti(II) Species," published in Organometallics 2004, 23, pp. 3309-3318.

Guérin et al., entitled "Synthesis, Structure, and Reactivity of the Phosphinimide Complexes $(\tau\text{-Bu}_3PN)_nMX_{4-n}$ (M=Ti, Zr)," published in Organometallics 2000, 19, pp. 2994-3000.

Hawkeswood et al., entitled "Steric Effects in Metathesis and Reduction Reactions of Phosphinimines With Catechol- and Pinacolboranes," published in Inorg. Chem. 2005, 44, pp. 4301-4308.

Hawkeswood et al., entitled "Synthesis and Characterization of Vanadium(V)-Phosphinimide Complexes," published in Inorg. Chem 2003, 42, pp. 5429-5433.

Hollink et al., entitled "Altering Molecular Weight Distributions: Benzyl-Phosphinimide Titanium Complexes as Ethylene Polymerization Catalysts," published in Can. J. Chem 82: 2004, pp. 1304-1313.

Hollink et al., entitled "Group IV Phosphinimide Amide Complexes," published in Can. J. Chem 82: 2004, pp. 1634-1639.

Hollink et al., entitled "The Effects of Activators on Zirconium Phosphinimide Ethylene Polymerization Catalysts," published in Organometallics 2004, 23, pp. 1562-1569.

Hollink et al., entitled "Ti and Zr Bidentate bis-Phiosphinimide Complexes," published in Dalton Trans., 2003, pp. 3968-3974.

Kickham et al., entitled "Divergent Pathways of C—H Bond Activation: Reactions of $(\tau\text{-Bu}_3PN)_2TiMe_2$ with Trimethylaluminum," published in J. Am. Chem. Soc. 2002, 124, pp. 11486-11494.

Kickham et al., entitled "Multiple C—H Bond Activation: Reactions of Titanium-Phosphinimide Complexes with Trimethylaluminum," published in Organometallics 2001, 20, pp. 1175-1182.

LePichon et al., entitled "Contrasting Formation of a (Phenylthio)phosphinimine and (Phenylthio)phosphazide. Synthesis of Metal Complexes," published in Inorg. Chem. 2001, 40, pp. 3827-3829.

LePichon et al., entitled "Iron Phosphinimide and Phosphinimine Complexes: Catalyst Precursors for Ethylene Polymerization," published in Organometallics 2002, 21, pp. 1362-1366.

Ma et al., entitled "Competitive ArC—H and ArC-X (X=Cl, Br) Activation in Halobenzenes at Cationic Titanium Centers," published in J. Am. Chem. Soc. 2006, 128, pp. 3303-3312.

Ma et al., entitled "Isolation and Characterization of a Monomeric Cationic Titanium Hydride," published in J. Am. Chem. Soc. 2004, 126, pp. 5668-5669.

Martinez et al., entitled "Monometallic, Homo-, and Hetero-Bimetallic Complexes of a Siloxy-bis(Phosphinimide) Ligand," published in Can. J. Chem 84, 2006, pp. 1180-1187.

(56) References Cited

OTHER PUBLICATIONS

McCahill et al., entitled "Copolymerization of Sterically Demanding Phosphine-Olefins and 1-Hexene," published in Can. J. Chem. 87, 2009, pp. 1620-1624.

Ong et al., entitled "Neutral and Cationic Group 13 Phosphinimine and Phosphinimide Complexes," published in Organometallics 1999, 18, pp. 4197-4204.

Ong et al., entitled "Synthesis, Structure, and Reactivity of Titanium Phosphinimide Thiolate Complexes," published in Organometallics 2002, 21, pp. 1646-1653.

Qi et al., entitled "Titanium Complexes with Novel Triaryl-Substituted Phosphinimide Ligands: Synthesis, Structure and Ethylene Polymerization Behavior," published in J. of Organometallic Chemistry, 2006, 691, pp. 1154-1158.

Ramos et al., entitled "Titanium Ferrocenyl-Phosphinimide Complexes," published in Dalton Trans., 2010, 39, pp. 1328-1338.

Stephan et al., entitled "An Approach to Catalyst Design: Cyclopentadienyl-Titanium Phosphinimide Complexes in Ethylene Polymerization," published in Organometallics 2003, 22, pp. 1937-1947.

Stephan et al., entitled "Phosphinimides as a Steric Equivalent to Cyclopentadienyl: An Approach to Ethylene Polymerization Catalyst Design," published in Organometallics 1999, 18, pp. 1116-1118.

Stephan et al., entitled "Remarkably Active Non-Metallocene Ethylene Polymerization Catalysts," published in Organometallics 1999, 18, pp. 2046-2048.

Stephan, Douglas W., entitled "The Road to Early-Transition-Metal Phosphinimide Olefin Polymerization Catalysts," published in Organometallics 2005, 24, pp. 2548-2560.

Sung et al., entitled "Synthesis, Structure, and Single-Crystal EPR Study of $[Cp(\upsilon-Bu_3PN)Ti(\mu-Cl)]_2$," published in Inorg. Chem. 2000, 39, pp. 2542-2546.

Voth et al., entitled "Functionalizing Titanium-Phosphinimide Complexes," published in Organometallics 2006, 25, pp. 4779-4786.

Wei et al., entitled Magnesium Complexes of Bis(phosphinimine)Methane and—Methanide Ligands, published in Organometallics 2003, 22, pp. 601-604.

Yadav et al., entitled "Phosphinimide Complexes With Pendant Hemilabile Donors: Synthesis, Structure and Ethylene Polymerization Activity†" published in Dalton Trans., 2009, pp. 1636-1643.

Yue et al., entitled "Phosphinimide-Phosphinimide Ligands: New Bulky Ligands for Ethylene Polymerization Catalysts," published in Organometallics 2001, 20, pp. 2303-2308.

Yue et al., entitled "Zirconium Phosphinimide Complexes: Synthesis, Structure, and Deactivation Pathways in Ethylene Polymerization Catalysis," published in Organometallics 2001, 20, pp. 4424-4433.

Film Extrusion Manual—Process, Materials, Properties, TAPPI Press, 1992, 16 pages.

Modern Plastics Encyclopedia, Mid-Nov. 1995 Issue, vol. 72, No. 12, 3 pages.

CATALYST SYSTEMS CONTAINING LOW VALENT TITANIUM COMPOUNDS AND POLYMERS PRODUCED THEREFROM

BACKGROUND OF THE INVENTION

Polyolefins such as high density polyethylene (HDPE) homopolymer and linear low density polyethylene (LLDPE) copolymer can be produced using various combinations of catalyst systems and polymerization processes. In some end-use applications, it can be beneficial for the catalyst system to produce polymers with high melt strength and a broad molecular weight distribution. Moreover, it can be beneficial for the catalyst system to provide control over the molecular weight distribution through the selection of a particular alkylaluminum reagent. Accordingly, it is to these ends that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to the preparation of new catalyst compositions, methods for preparing the catalyst compositions, methods for using the catalyst compositions to polymerize olefins, the polymer resins produced using such catalyst compositions, and articles produced using these polymer resins. In particular, the present invention relates to bimetallic titanium compounds, and to catalyst compositions employing such compounds. Catalyst compositions of the present invention that contain these bimetallic titanium compounds can be used to produce, for example, ethylene-based homopolymers and copolymers.

In accordance with an aspect of the present invention, disclosed and described herein are bimetallic titanium compounds and methods for making bimetallic titanium compounds. Such bimetallic compounds can have the formula:

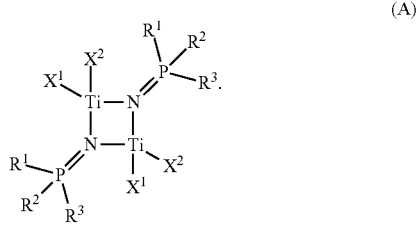

(A)

The bimetallic compounds having formula (A) can be synthesized in a method that comprises contacting a half-metallocene titanium compound having the formula:

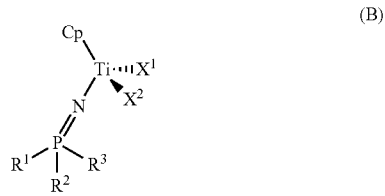

(B)

with an alkylaluminum compound having the formula $Al(R^Z)_3$ to form a mixture comprising the bimetallic compound having formula (A). In these formulas, $X^1$ and $X^2$ independently can be a halide; $R^1$, $R^2$, and $R^3$ independently can be H or a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group; Cp can be a substituted or unsubstituted cyclopentadienyl, indenyl, or fluorenyl group; and each $R^Z$ independently can be a $C_1$ to $C_{10}$ alkyl group.

Catalyst compositions containing bimetallic titanium compounds of formula (A) also are provided by the present invention, as well as processes for preparing the catalyst compositions. In one aspect, a catalyst composition is disclosed which comprises a bimetallic titanium compound of formula (A) and an activator. Optionally, this catalyst composition can further comprise a co-catalyst, such as an organoaluminum compound. In some aspects, the activator can comprise an activator-support, while in other aspects, the activator can comprise an aluminoxane compound, an organoboron or organoborate compound, an ionizing ionic compound, or combinations thereof.

The present invention also contemplates and encompasses olefin polymerization processes. Such processes can comprise contacting a catalyst composition with an olefin monomer and optionally an olefin comonomer in a polymerization reactor system under polymerization conditions to produce an olefin polymer. Generally, the catalyst composition employed can comprise any of the bimetallic titanium compounds disclosed herein and any of the activators disclosed herein. Further, organoaluminum compounds or other co-catalysts also can be utilized in the catalyst compositions and/or polymerization processes.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

DEFINITIONS

Figure 1:
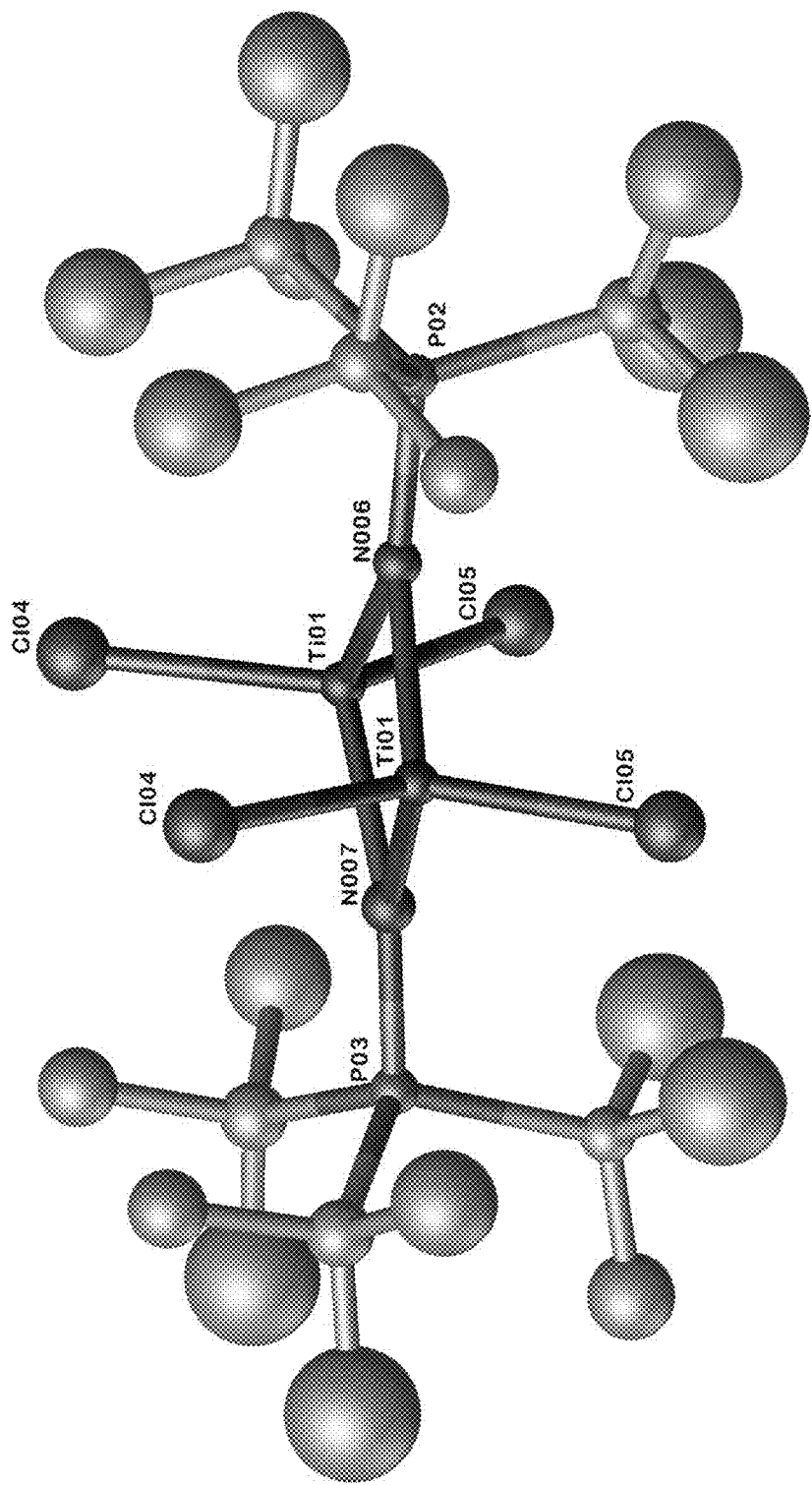
FIG. 1 illustrates the crystal structure of the bimetallic titanium compound of Example A.
Figure 2:
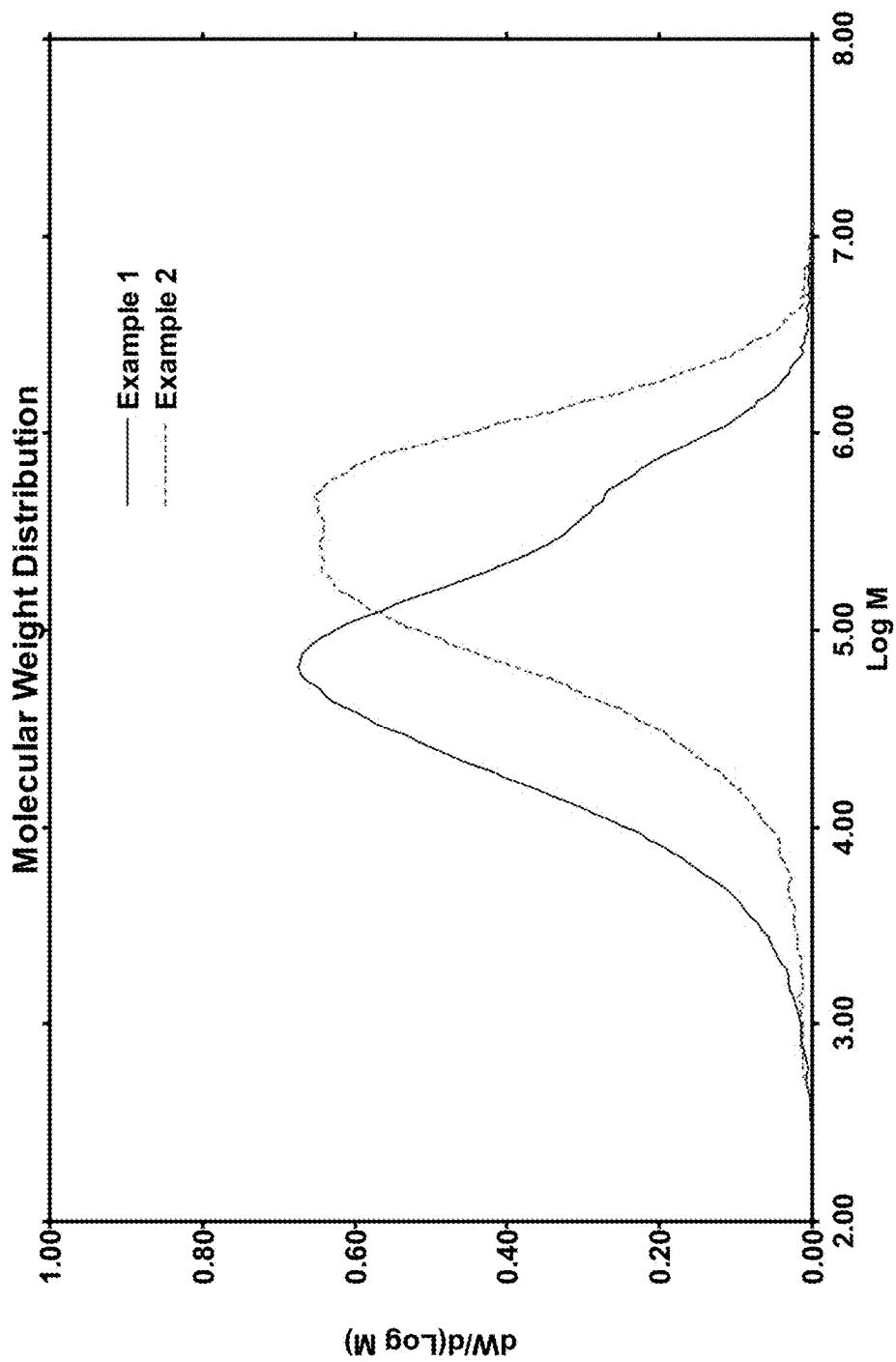
FIG. 2 presents a plot of the molecular weight distributions of the copolymers of Examples 1-2.
Figure 3:
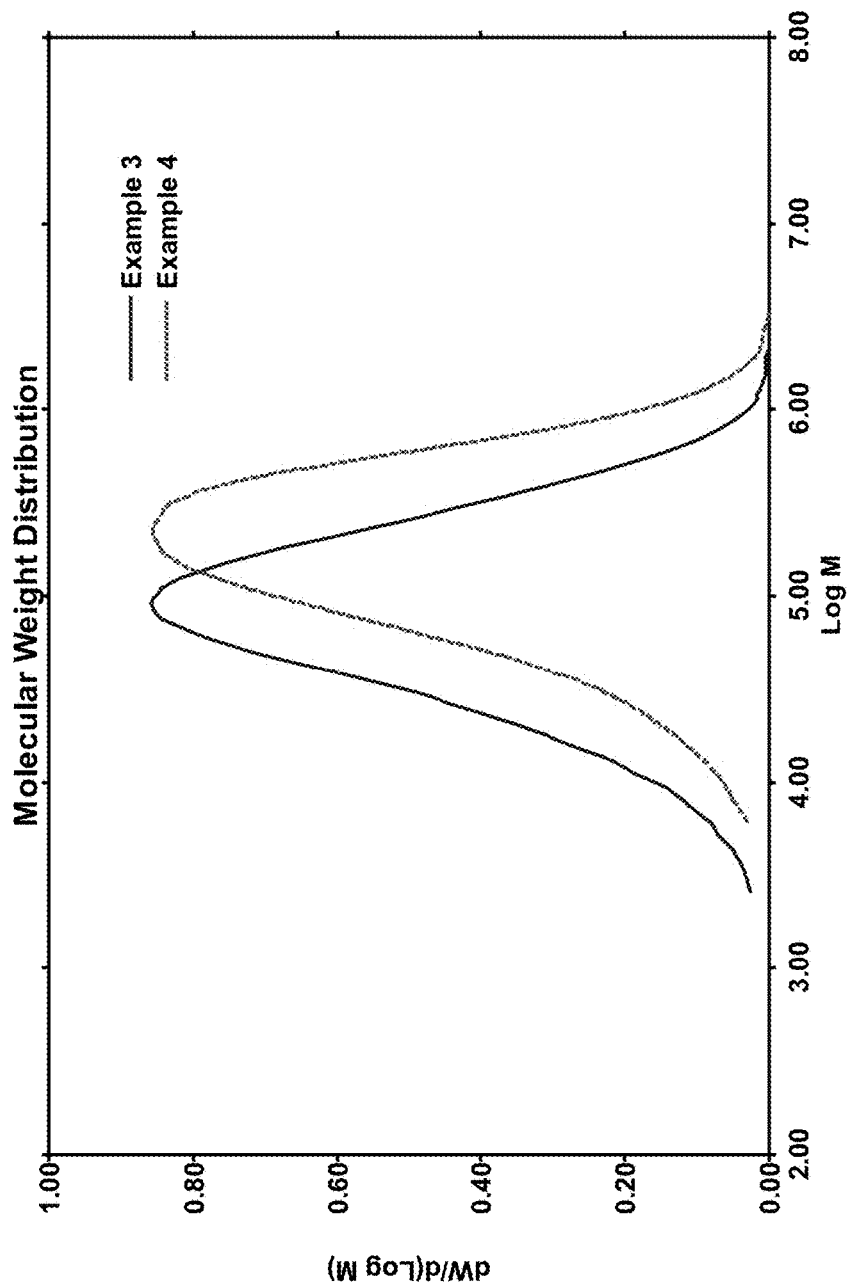
FIG. 3 presents a plot of the molecular weight distributions of the copolymers of Examples 3-4.
Figure 4:
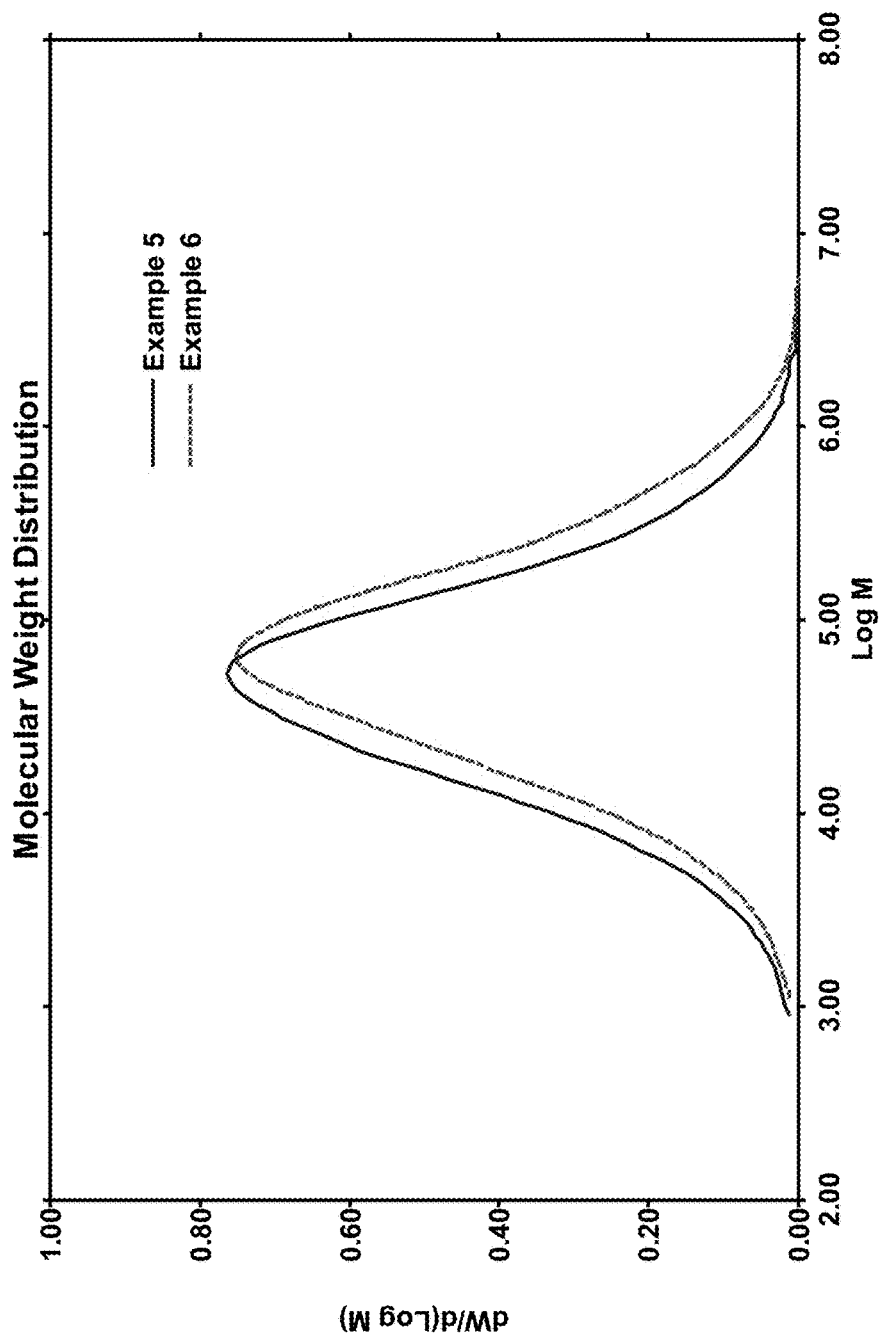
FIG. 4 presents a plot of the molecular weight distributions of the copolymers of Examples 5-6.
Figure 5:
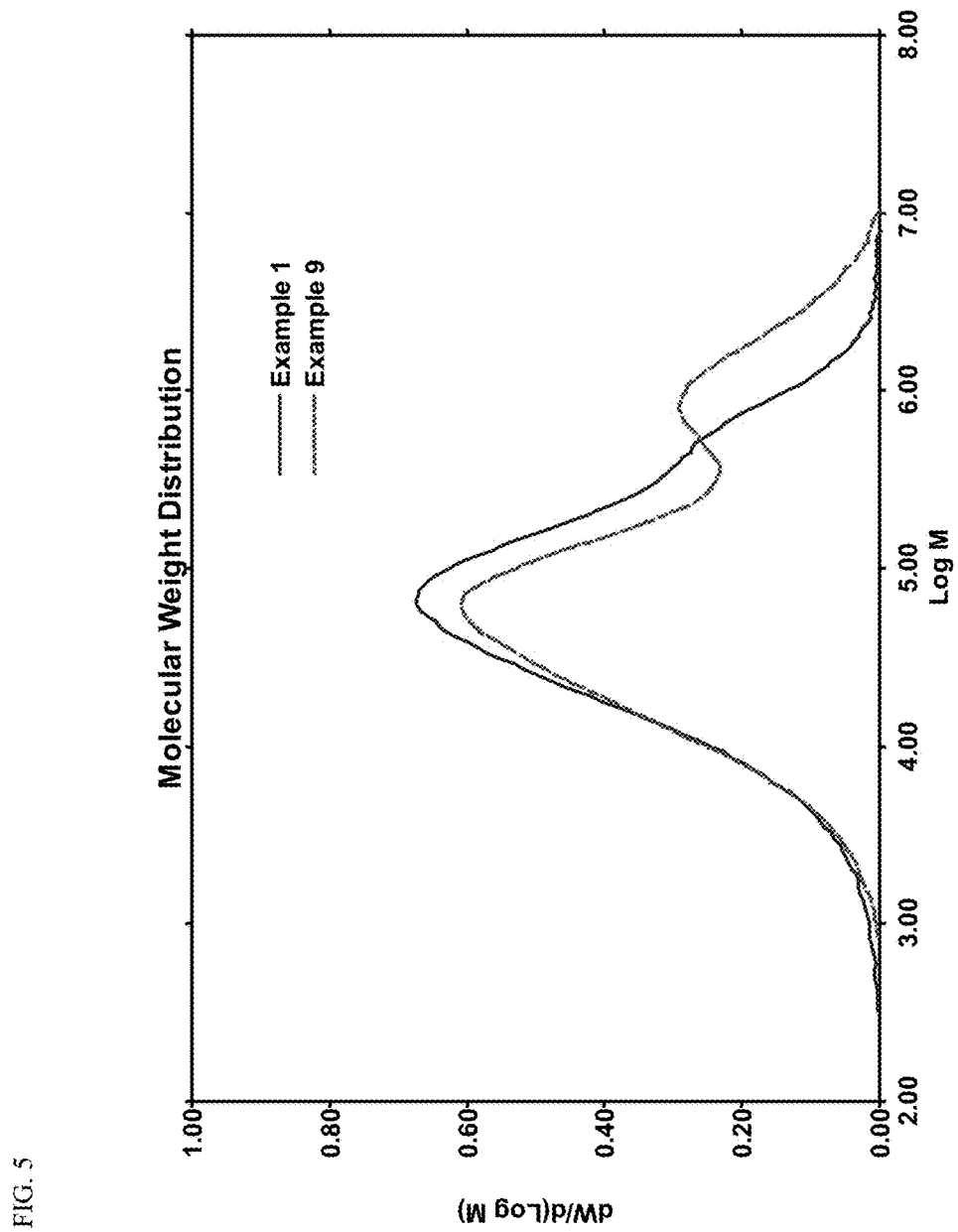
FIG. 5 presents a plot of the molecular weight distributions of the copolymers of Examples 1 and 9.
Figure 6:
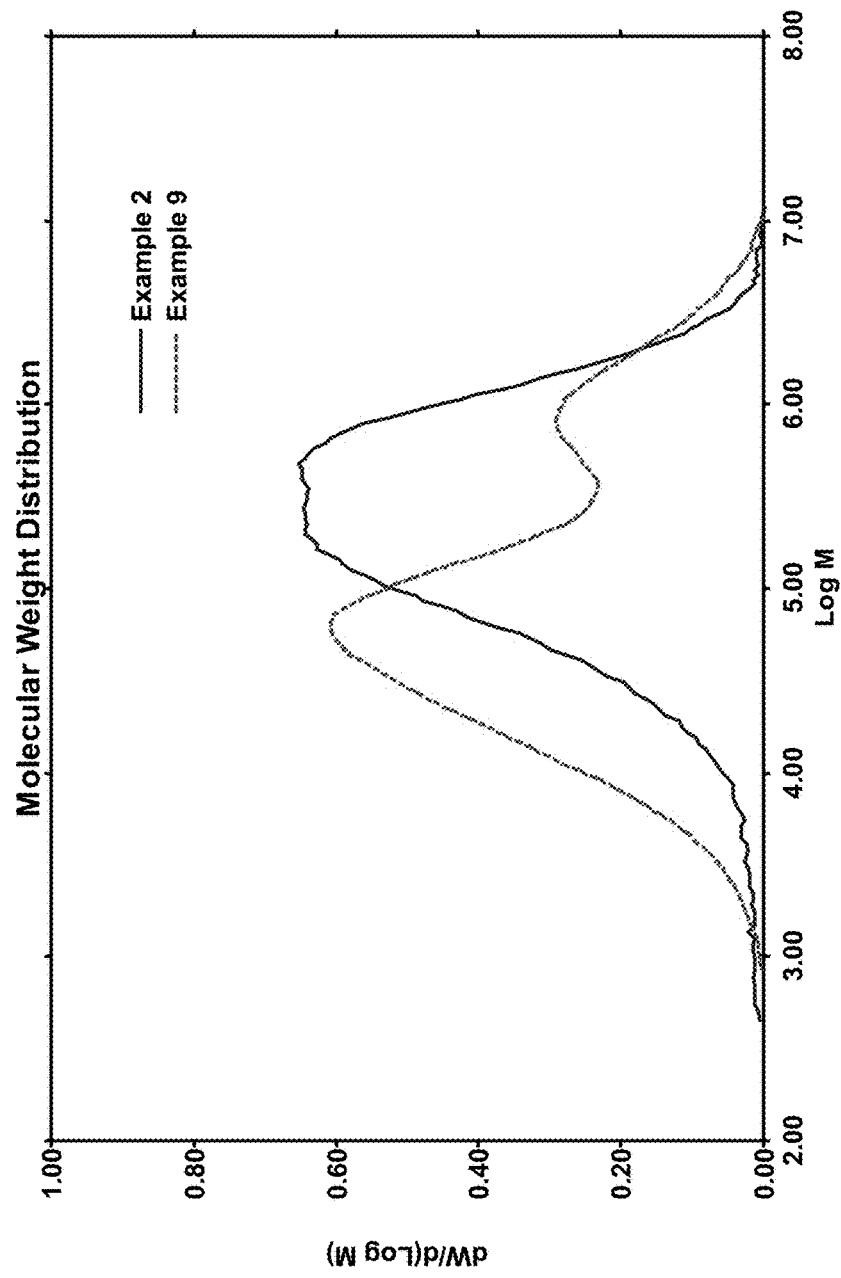
FIG. 6 presents a plot of the molecular weight distributions of the copolymers of Examples 2 and 9.
Figure 7:
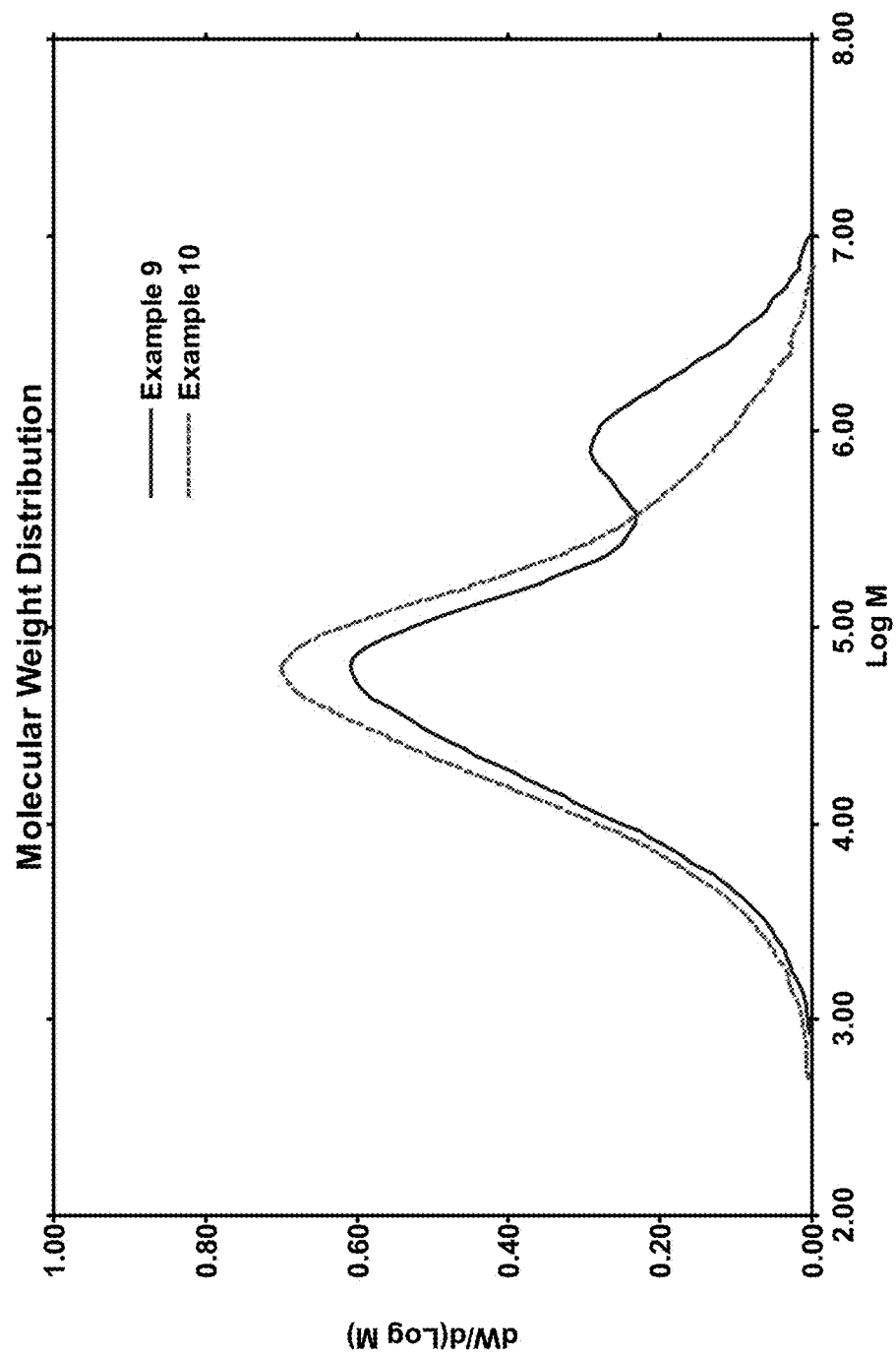
FIG. 7 presents a plot of the molecular weight distributions of the copolymers of Examples 9-10.
Figure 8:
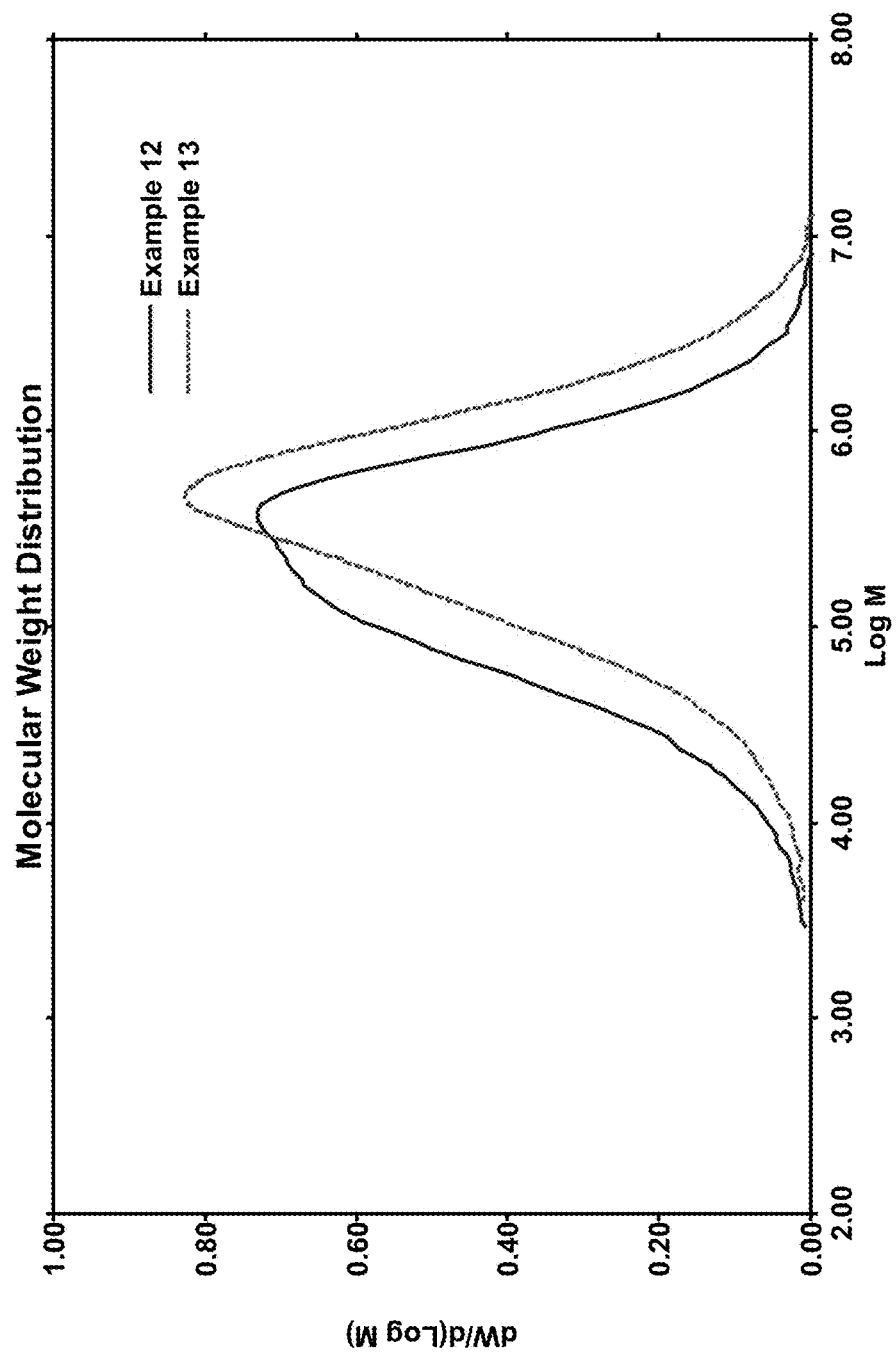
FIG. 8 presents a plot of the molecular weight distributions of the copolymers of Examples 12-13.
Figure 9:
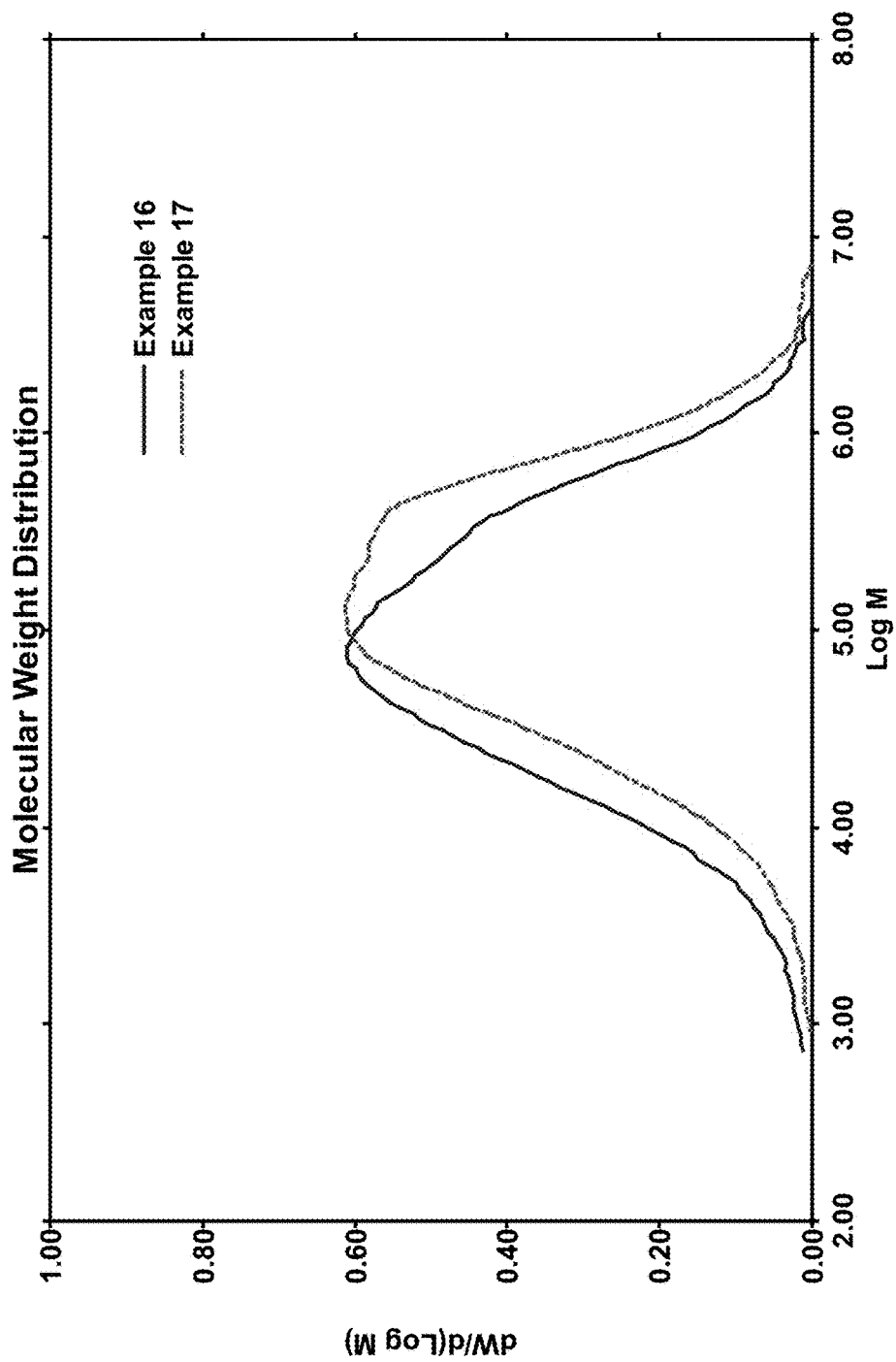
FIG. 9 presents a plot of the molecular weight distributions of the copolymers of Examples 16-17.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of; a bimetallic titanium compound, an activator, and optionally, a co-catalyst.

The terms "a," "an," "the," etc., are intended to include plural alternatives, e.g., at least one, unless otherwise specified. For instance, the disclosure of "an activator-support" or "a bimetallic titanium compound" is meant to encompass one, or mixtures or combinations of more than one, activator-support or bimetallic titanium compound, respectively, unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any compound(s) disclosed herein, the structure or name presented is also intended to encompass all structural isomers, conformational isomers, and stereoisomers that can arise from a particular set of substituents, or the binding of different enantiotopic faces of a cyclopentadienyl-type ligand (e.g., substituted cyclopentadienyl, indenyl, substituted fluorenyl, etc.) to a metal atom, unless indicated otherwise. Thus, a general reference to a compound includes all structural isomers unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general or specific structure or name encompasses all enantiomers, diastereomers, and other optical isomers whether in enantiomeric or racemic forms, as well as mixtures of stereoisomers, as the context permits or requires.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

The term "polymer" is used herein generically to include olefin homopolymers, copolymers, terpolymers, and so forth, as well as alloys and blends thereof. The term "polymer" also includes all possible geometrical configurations, unless stated otherwise, and such configurations can include isotactic, syndiotactic, and random symmetries. The term "polymer" also includes impact, block, graft, random, and alternating copolymers. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer can be categorized an as ethylene/1-hexene copolymer.

In like manner, the scope of the term "polymerization" includes homopolymerization, copolymerization, terpolymerization, etc. Therefore, a copolymerization process can involve contacting one olefin monomer (e.g., ethylene) and one olefin comonomer (e.g., 1-hexene) to produce a copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used, for example, in addition to an activator-support. The term "co-catalyst" is used regardless of the actual function of the compound or any chemical mechanism by which the compound may operate.

The term "activator-support" is used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the activator-support can comprise a calcined contact product of at least one solid oxide with at least one electron-withdrawing anion source compound. The terms "support" and "activator-support" are not used to imply these components are inert, and such components should not be construed as an inert component of the catalyst composition. The term "activator," as used herein, refers generally to a substance that is capable of converting a titanium component into a catalyst that can polymerize olefins, or converting a contact product of a bimetallic titanium component and a component that provides an activatable ligand (e.g., an alkyl, a hydride) to the bimetallic titanium, when the bimetallic titanium compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the co-catalyst, the bimetallic titanium compound, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "contact product" is used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. This term encompasses mixtures, blends, solutions, slurries, reaction products, and the like, as well as combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner.

The terms Mn, Mw, and Mz, as used herein, are defined as follows: Mn: number-average molecular weight; Mw: weight-average molecular weight; Mz: z-average molecular weight. These values are determined by calculations on the basis of molecular weight distribution curves determined using gel permeation chromatography (GPC), also known as size-exclusion chromatography (SEC).

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the ratio of Mw/Mn of an ethylene polymer consistent with aspects of this invention. By a disclosure that the ratio of Mw/Mn can be in a range from about 2 to about 18, the intent is to recite that the ratio of Mw/Mn can be any ratio in the range and, for example, can be equal to about 2, about 3, about 4, about 5, about 6, about 7, about 8, about 9, about 10, about 11, about 12, about 13, about 14, about 15, about 16, about 17, or about 18. Additionally, the ratio of Mw/Mn can be within any range from about 2 to about 18 (for example, from about 2 to about 10), and this also includes any combination of ranges between about 2 and about 18 (for example, the Mw/Mn ratio can be in a range from about 3 to about 9, or from about 11 to about 15). Likewise, all other ranges disclosed herein should be interpreted in a manner similar to these examples.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

DETAILED DESCRIPTION OF THE INVENTION

The present invention is directed generally to bimetallic titanium compounds, methods of making the bimetallic titanium compounds, catalyst compositions employing the bimetallic titanium compounds, methods for preparing the catalyst compositions, methods for using the catalyst compositions to polymerize olefins, the polymer resins produced using such catalyst compositions, and articles produced using these polymer resins.

Bimetallic Titanium Compounds

Disclosed herein are bimetallic titanium compounds and methods of making these compounds. The bimetallic titanium compounds can have the following formula:

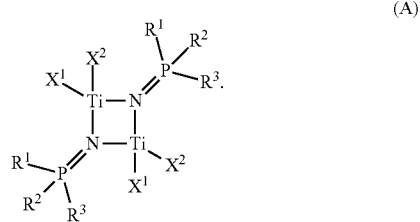

(A)

Within formula (A), $R^1$, $R^2$, $R^3$, $X^1$, and $X^2$ are independent elements of the bimetallic titanium compound. Accordingly, the bimetallic titanium compound having formula (A) can be described using any combination of $R^1$, $R^2$, $R^3$, $X^1$, and $X^2$ disclosed herein.

Unless otherwise specified, formula (A) above, any other structural formulas disclosed herein, and any bimetallic titanium compound or species disclosed herein are not designed to show stereochemistry or isomeric positioning of the different moieties (e.g., these formulas are not intended to display rac or meso isomers, or R or S diastereoisomers), although such compounds are contemplated and encompassed by these formulas and/or structures, unless stated otherwise.

In accordance with aspects of this invention, $X^1$ and $X^2$ in formula (A) independently can be a halide (e.g., F, Cl, Br, etc.). It is contemplated that $X^1$ and $X^2$ can be either the same or a different halide. In some aspects, both $X^1$ and $X^2$ are Cl.

In formula (A), $R^1$, $R^2$, and $R^3$ can be any suitable substituent. For instance, $R^1$, $R^2$, and $R^3$ independently can be H or a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group. It is contemplated that $R^1$, $R^2$, and $R^3$ can be the same or different. In one aspect, $R^1$, $R^2$, and $R^3$ independently can be H, a halide, a $C_1$ to $C_{18}$ hydrocarbyl group, a $C_1$ to $C_{18}$ halogenated hydrocarbyl group, a $C_1$ to $C_{18}$ hydrocarboxy group, or a $C_1$ to $C_{18}$ hydrocarbylsilyl group. In another aspect, $R^1$, $R^2$, and $R^3$ independently can be H, a halide, a $C_1$ to $C_{12}$ hydrocarbyl group, a $C_1$ to $C_{12}$ halogenated hydrocarbyl group, a $C_1$ to $C_{12}$ hydrocarboxy group, or a $C_1$ to $C_{12}$ hydrocarbylsilyl group. In yet another aspect, $R^1$, $R^2$, and $R^3$ independently can be H, a halide, a $C_1$ to $C_8$ hydrocarbyl group, a $C_1$ to $C_8$ halogenated hydrocarbyl group, a $C_1$ to $C_8$ hydrocarboxy group, or a $C_1$ to $C_8$ hydrocarbylsilyl group.

$R^1$, $R^2$, and $R^3$ independently can be H or a $C_1$ to $C_{18}$ hydrocarbyl group in certain aspects of this invention. For instance, $R^1$, $R^2$, and $R^3$ in formula (A) can independently be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, $R^1$, $R^2$, and $R^3$ independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, $R^1$, $R^2$, and $R^3$ independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, $R^1$, $R^2$, and $R^3$ independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be any of $R^1$, $R^2$, and $R^3$ in formula (A) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be any of $R^1$, $R^2$, and $R^3$ in formula (A) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. Alternatively, $R^1$, $R^2$, and $R^3$ independently can be a $C_1$ to $C_8$ alkyl group.

Suitable alkenyl groups which can be any of $R^1$, $R^2$, and $R^3$ in formula (A) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, $R^1$, $R^2$, and $R^3$ in formula (A) independently can be an ethenyl group, a propenyl group, a butenyl group, a pentenyl group, a hexenyl group, a heptenyl group, an octenyl group, a nonenyl group, or a decenyl group, while in another aspect, $R^1$, $R^2$, and $R^3$ in formula (A) independently can be an ethenyl group, a propenyl group, a butenyl group, a pentenyl group, or a hexenyl group. For example, any of $R^1$, $R^2$, and $R^3$ can be an ethenyl group; alternatively, a propenyl group; alternatively, a butenyl group; alternatively, a pentenyl group; or alternatively, a hexenyl group. In yet another aspect, any of $R^1$, $R^2$, and $R^3$ can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. For example, in some aspects, at least one of $R^1$, $R^2$, and $R^3$ is a $C_3$ to $C_{12}$ alkenyl group, or a $C_3$ to $C_{12}$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

Any of $R^1$, $R^2$, and $R^3$ in formula (A) independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, any of $R^1$, $R^2$, and $R^3$ in formula (A) can be a cyclopentyl group, a substituted cyclopentyl group, a cyclohexyl group, or a substituted cyclohexyl group. Moreover, $R^1$, $R^2$, and $R^3$ in formula (A) independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be any of $R^1$, $R^2$, and $R^3$ in formula (A).

In some aspects, the aryl group which can be any of $R^1$, $R^2$, and $R^3$ in formula (A) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be any of $R^1$, $R^2$, and $R^3$ in formula (A).

In an aspect, the substituted phenyl group which can be any of $R^1$, $R^2$, and $R^3$ in formula (A) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be any of $R^1$, $R^2$, and $R^3$ in formula (A).

In some aspects, the aralkyl group which can be any of $R^1$, $R^2$, and $R^3$ in formula (A) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be any of $R^1$, $R^2$, and $R^3$ in formula (A).

In an aspect, each non-hydrogen substituent(s) for the substituted cycloalkyl group, substituted aryl group, or substituted aralkyl group which can be any of $R^1$, $R^2$, and $R^3$ in formula (A) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be any of $R^1$, $R^2$, and $R^3$ in formula (A). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

Any of $R^1$, $R^2$, and $R^3$ in formula (A) independently can be, in certain aspects, a $C_1$ to $C_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be any of $R^1$, $R^2$, and $R^3$ in formula (A) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be any of $R^1$, $R^2$, and $R^3$ in formula (A) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

In accordance with some aspects disclosed herein, any of $R^1$, $R^2$, and $R^3$ in formula (A) can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). As used herein, hydrocarbylsilyl is intended to cover (mono)hydrocarbylsilyl (—SiH$_2$R), dihydrocarbylsilyl (—SiHR$_2$), and trihydrocarbylsilyl (—SiR$_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be any of $R^1$, $R^2$, and $R^3$ in formula (A) can include, but are not limited to, trimethylsilyl, triethylsilyl, tripropyl silyl (e.g., triisopropylsilyl), tributyl silyl, tripentyl silyl, triphenyl silyl, allyldimethylsilyl, and the like.

In some aspects, $R^1$, $R^2$, and $R^3$ independently can be H, Cl, CF$_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a 2,6-diisopropylphenyl group, a tolyl group, a benzyl group, a naphthyl group, a trimethylsilyl group, a triisopropylsilyl group, a triphenylsilyl group, or an allyldimethylsilyl group.

An illustrative and non-limiting example of a bimetallic titanium compound having formula (A) is the following compound (t-Bu=tert-butyl):

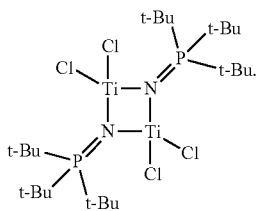

Synthesis of Bimetallic Titanium Compounds

Methods of making bimetallic titanium compounds having formula (A) also are disclosed herein. Such methods can comprise contacting a half-metallocene titanium compound having the formula:

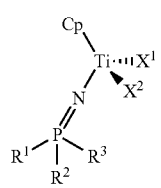

with an alkylaluminum compound having the formula Al(R$^Z$)$_3$ to form a mixture comprising the bimetallic compound having formula (A):

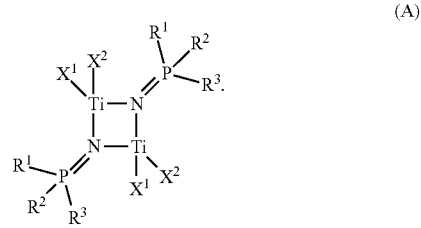

The selections for $R^1$, $R^2$, $R^3$, $X^1$, and $X^2$ in formula (B) can be the same as those described hereinabove for formula (A) as it pertains to the bimetallic titanium compound. For instance, $R^1$, $R^2$, and $R^3$ independently can be H or a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group; alternatively, $R^1$, $R^2$, and $R^3$ independently can be H or a $C_1$ to $C_{18}$ hydrocarbyl group; or alternatively, $R^1$, $R^2$, and $R^3$ independently can be a $C_1$ to $C_8$ alkyl group. Likewise, $X^1$ and $X^2$ in formula (B) can be a halide, and in some instances, both $X^1$ and $X^2$ in formula (B) can be Cl (if $X^1$ and $X^2$ are not halides—for instance, hydrocarbyl groups (e.g., methyl or benzyl)—the bimetallic titanium compound of formula (A) is not formed). Moreover, any bimetallic titanium compounds produced in accordance with this method are encompassed herein.

Cp in formula (B) can be a substituted or unsubstituted cyclopentadienyl group, indenyl group, or fluorenyl group. Hence, Cp can be unsubstituted or can be substituted with any suitable substituent, any suitable number of substituents, and at any suitable position(s) that conforms to the rules of chemical valence. In one aspect, for instance, Cp can be a cyclopentadienyl group, while in another aspect, Cp can be an indenyl group, and in yet another aspect, Cp can be a fluorenyl group. In these and other aspects, Cp can be unsubstituted.

Alternatively, Cp can contain a substituent (one or more), such as H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. The halide, $C_1$ to $C_{36}$ hydrocarbyl group, $C_1$ to $C_{36}$ halogenated hydrocarbyl group, $C_1$ to $C_{36}$ hydrocarboxy group, and $C_1$ to $C_{36}$ hydrocarbylsilyl group which can be a substituent on Cp in formula (B) can be any halide, $C_1$ to $C_{36}$ hydrocarbyl group, $C_1$ to $C_{36}$ halogenated hydrocarbyl group, $C_1$ to $C_{36}$ hydrocarboxy group, and $C_1$ to $C_{36}$ hydrocarbylsilyl group described herein (e.g., as pertaining to $X^1$, $X^2$, $R^1$, $R^2$, and/or $R^3$ in formula (A)).

Thus, each substituent independently can be H; alternatively, a halide; alternatively, H or a $C_1$ to $C_{12}$ hydrocarbyl group; alternatively, a $C_1$ to $C_{12}$ halogenated hydrocarbyl group; alternatively, a $C_1$ to $C_{12}$ hydrocarboxy group; alternatively, a $C_1$ to $C_{12}$ hydrocarbylsilyl group; alternatively, a $C_1$ to $C_{12}$ hydrocarbyl group or a $C_1$ to $C_{12}$ hydrocarbylsilyl group; or alternatively, a $C_1$ to $C_8$ alkyl group or a $C_3$ to $C_8$ alkenyl group. As a non-limiting example, each substituent on Cp independently can be H, Cl, CF$_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group (or other substituted aryl group), a benzyl group, a naphthyl group, a trimethylsilyl group, a triisopropylsilyl group, a triphenylsilyl group, an allyldimethylsilyl group, or a 1-methylcyclohexyl group; alternatively, H; alternatively, Cl; alternatively, $CF_3$; alternatively, a methyl group; alternatively, an ethyl group; alternatively, a propyl group; alternatively, a butyl group; alternatively, a pentyl group; alternatively, a hexyl group; alternatively, a heptyl group; alternatively, an octyl group, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; alternatively, a benzyl group; alternatively, a naphthyl group; alternatively, a trimethylsilyl group; alternatively, a triisopropylsilyl group; alternatively, a triphenylsilyl group; alternatively, an allyldimethylsilyl group; or alternatively, a 1-methylcyclohexyl group.

Unexpectedly, the Cp group in formula (B) can be cleaved from the titanium metal in the methods of synthesizing the bimetallic titanium compounds having formula (A) disclosed herein.

Consistent with the methods disclosed herein, the half-metallocene titanium compound having formula (B) can be contacted (or reacted) with an alkylaluminum compound having the formula $Al(R^Z)_3$. In this formula, each $R^Z$ independently can be a $C_1$ to $C_{10}$ alkyl group; alternatively, a $C_1$ to $C_8$ alkyl group; alternatively, a $C_1$ to $C_6$ alkyl group; or alternatively, a $C_1$ to $C_4$ alkyl group. In an aspect, each $R^Z$ independently can be a methyl group, an ethyl group, a propyl group, a butyl group (e.g., n-butyl or iso-butyl), a pentyl group, a hexyl group, a heptyl group, or an octyl group; alternatively, a methyl group, an ethyl group, a propyl group, a butyl group, a pentyl group, or a hexyl group; alternatively, a methyl group; alternatively, an ethyl group; alternatively, a propyl group; or alternatively, a butyl group. If DEAC (diethylaluminum chloride) or a similar compound is used, the bimetallic titanium compound of formula (A) is not formed. Accordingly, the alkylaluminum compound can comprise (or consist essentially of, or consist of) trimethylaluminum (TMA), triethylaluminum (TEA), tri-n-propyl-aluminum (TNPA), tri-n-butylaluminum (TNBA), triisobutylaluminum (TIBA), tri-n-hexylaluminum, tri-n-octylaluminum, and the like, or combinations thereof. In one aspect, the alkylaluminum compound can comprise (or consist essentially of, or consist of) trimethylaluminum, triethylaluminum, triisobutylaluminum, or a combination thereof. In another aspect, the alkylaluminum compound can comprise (or consist essentially of, or consist of) trimethylaluminum; alternatively, triethylaluminum; alternatively, tri-n-propylaluminum; alternatively, tri-n-butyl aluminum; alternatively, triisobutylaluminum; alternatively, tri-n-hexylaluminum; or alternatively, tri-n-octylaluminum.

While not being limited thereto, the molar ratio (Al:Ti) of the alkylaluminum compound to the half-metallocene titanium compound often can fall within a range of from about 0.5:1 to about 10:1. For instance, the minimum molar ratio of the alkylaluminum compound to the half-metallocene titanium compound can be about 0.5:1, about 0.8:1, about 0.9:1, about 1:1, about 1.1:1, about 1.2:1, or about 1.5:1; additionally or alternatively, the maximum molar ratio of the alkylaluminum compound to the half-metallocene titanium compound can be about 10:1, about 5:1, about 3:1, or about 2:1. Generally, the molar ratio of the alkylaluminum compound to the half-metallocene titanium compound can be in a range from any minimum molar ratio disclosed herein to any maximum molar ratio disclosed herein. Therefore, suitable non-limiting ranges for the molar ratio of the alkylaluminum compound to the half-metallocene titanium compound can include the following ranges: from about 0.5:1 to about 10:1, from about 0.9:1 to about 10:1, from about 1:1 to about 5:1, from about 1.1:1 to about 3:1, or from about 1.1 to about 2:1. In some aspects, the molar ratio can be equal to about 1:1 (stoichiometric). Other appropriate ranges for the molar ratio of the alkylaluminum compound to the half-metallocene titanium compound are readily apparent from this disclosure. If more than one alkylaluminum compound and/or more than one half-metallocene titanium compound is/are employed, this ratio is based on the total molar amounts of the respective components.

The contacting (or reacting) of the half-metallocene titanium compound having formula (B) with the alkylaluminum—also referred to herein as a pre-reduction step—to form the mixture containing the bimetallic compound is not limited to any particular temperature. Typically, however, the contacting step and the formation of the bimetallic compound may be performed at a temperature in a range from about 0° C. to about 120° C.; alternatively, from about 0° C. to about 80° C.; alternatively, from about 10° C. to about 60° C.; alternatively, from about 10° C. to about 35° C.; or alternatively, from about 20° C. to about 40° C. In these and other aspects, these temperature ranges also are meant to encompass circumstances where the contacting step and the formation of the bimetallic compound are conducted at a series of different temperatures, instead of at a single fixed temperature, falling within the respective ranges.

Similarly, the time required for the contacting step and the formation of the bimetallic compound is not limited to any particular period of time. Whether a particular time period is suitable can depend upon, for example, the molar ratio of the alkylaluminum compound to the half-metallocene titanium compound, the temperature at which the components are contacted and the mixture is formed, the presence of diluents or solvents, and the degree of mixing, among other variables. Typically, however, a minimum period of time for the contacting step can be about 1 minute, about 15 minutes, about 30 minutes, about 1 hour, or about 2 hours; additionally or alternatively, a maximum suitable period of time for the contacting step can be about 96 hours, about 48 hours, about 36 hours, about 30 hours, about 24 hours, about 18 hours, about 12 hours, about 6 hours, or about 4 hours. Generally, the time period used the contacting step and the formation of the bimetallic compound can be in a range from any minimum time period disclosed herein to any maximum time period disclosed herein. Accordingly, suitable non-limiting ranges can include the following: from about 1 minute to about 96 hours, from about 15 minutes to about 48 hours, from about 30 minutes to about 36 hours, from about 1 hour to about 30 hours, or from about 2 hours to about 24 hours. Other suitable time periods are readily apparent from this disclosure.

The time period used in the pre-reduction step can be any length of time sufficient to reduce at least a portion of the half-metallocene titanium(IV) compound to any titanium (III) species, such as a bimetallic titanium(III) compound (e.g., formula (A)). Further, the time period used in the pre-reduction step can impact the amount of Ti(IV) species remaining in the mixture, where a longer time period generally results in less residual Ti(IV) compounds. While not wishing to be bound by the following theory, it is believed that for time periods of up to 1 hour (depending upon other reaction conditions, of course), a mixture of Ti(III) and Ti(IV) species can be present; after 1 hour, it is believed that effectively all of the Ti(IV) has reacted (assuming an excess of the alkylaluminum compound is present). Accordingly, in some aspects of this invention, a suitable time period can be any period of time sufficient for the mixture to be substantially free of Ti(IV) compounds, i.e., to contain less than 10 wt. % of Ti(IV) compounds. For instance, the time period used in the contacting step and formation of the bimetallic compound can be a period of time sufficient for the mixture to contain less than about 8 wt. %, less than about 5 wt. %, less than about 3 wt. %, less than about 1 wt. %, less than about 0.5 wt. %, or less than about 0.1 wt. %, of Ti(IV) compounds.

Thus, in some aspects of the invention, the mixture containing the bimetallic titanium compound of formula (A) can be substantially free of Ti(IV) compounds (i.e., contain less than 10 wt. %), and in some circumstances, can contain less than about 8 wt. %, less than about 5 wt. %, less than about 3 wt. %, less than about 1 wt. %, less than about 0.5 wt. %, or less than about 0.1 wt. %, of Ti(IV) compounds).

Additionally, the mixture containing the bimetallic titanium compound of formula (A) can further comprise Ti(II) compounds, can further comprise additional Ti(III) compounds, or can further comprise Ti(II) compounds and additional Ti(III) compounds (other than the bimetallic compound of formula (A)).

Catalyst Compositions

In some aspects, the present invention employs catalyst compositions comprising a bimetallic titanium compound and an activator. These catalyst compositions can be utilized to produce polyolefins—homopolymers, copolymers, and the like—for a variety of end-use applications. Bimetallic titanium compounds and methods of their synthesis are discussed hereinabove. In aspects of the present invention, it is contemplated that the catalyst composition can contain more than one bimetallic titanium compound. Further, additional catalytic compounds—other than those specified as a bimetallic titanium compound—can be employed in the catalyst compositions and/or the polymerization processes, provided that the additional catalytic compound does not detract from the advantages disclosed herein. Additionally, more than one activator also can be utilized.

Generally, catalyst compositions of the present invention comprise a bimetallic titanium compound having formula (A) and an activator. Optionally, such catalyst compositions can further comprise one or more than one co-catalyst compound or compounds (suitable co-catalysts, such as organoaluminum compounds, also are discussed herein). In aspects of the invention, the activator can comprise an activator-support (e.g., an activator-support comprising a solid oxide treated with an electron-withdrawing anion). Activator-supports useful in the present invention are disclosed herein. Thus, a catalyst composition of this invention can comprise a bimetallic titanium compound, an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, or combinations thereof; or alternatively, a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Moreover, the organoaluminum compound can be the same as or different from the alkylaluminum compound used to synthesize the compound having formula (A). Accordingly, a catalyst composition consistent with aspects of the invention can comprise (or consist essentially of, or consist of) a bimetallic titanium compound; sulfated alumina (or fluorided-chlorided silica-coated alumina, or fluorided silica-coated alumina); and triethylaluminum (or triisobutylaluminum).

In another aspect of the present invention, a catalyst composition is provided which comprises a bimetallic titanium compound, an activator-support, and an organoaluminum compound, wherein this catalyst composition is substantially free of aluminoxanes, organoboron or organoborate compounds, ionizing ionic compounds, or combinations thereof; alternatively, substantially free of aluminoxanes; alternatively, substantially free or organoboron or organoborate compounds; or alternatively, substantially free of ionizing ionic compounds. In these aspects, the catalyst composition has catalyst activity, discussed below, in the absence of these additional materials. For example, a catalyst composition of the present invention can consist essentially of a bimetallic titanium compound, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a bimetallic titanium compound and an activator-support can further comprise an optional co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof; or alternatively, organoaluminum compounds, organozinc compounds, organomagnesium compounds, organolithium compounds, or any combination thereof. More than one co-catalyst can be present in the catalyst composition.

In a different aspect, a catalyst composition is provided which does not require an activator-support. Such a catalyst composition can comprise a bimetallic titanium compound, an activator, and an optional co-catalyst, wherein the activator can comprise an aluminoxane compound (e.g., a supported aluminoxane), an organoboron or organoborate compound, an ionizing ionic compound, or combinations thereof; alternatively, an aluminoxane compound; alternatively, an organoboron or organoborate compound; or alternatively, an ionizing ionic compound.

In a particular aspect contemplated herein, the catalyst composition is a catalyst composition comprising an activator (one or more than one) and only one bimetallic titanium compound having formula (A). In these and other aspects, the catalyst composition can comprise an activator (e.g., an activator-support comprising a solid oxide treated with an electron-withdrawing anion), only one bimetallic titanium metallocene compound, and a co-catalyst (one or more than one), such as an organoaluminum compound.

Alternatively, the catalyst composition can further contain a metallocene catalyst component. Any metallocene component of the catalyst systems provided herein can, in some aspects, comprise an unbridged metallocene; alternatively, an unbridged zirconium or hafnium based metallocene compound; alternatively, an unbridged zirconium or hafnium based metallocene compound containing two cyclopentadienyl groups, two indenyl groups, or a cyclopentadienyl and an indenyl group; alternatively, an unbridged zirconium based metallocene compound containing two cyclopentadienyl groups, two indenyl groups, or a cyclopentadienyl and an indenyl group. Illustrative and non-limiting examples of unbridged metallocene compounds (e.g., with zirconium or hafnium) that can be employed in catalyst systems consistent with aspects of the present invention are described in U.S. Pat. Nos. 7,199,073, 7,226,886, 7,312,283, and 7,619,047, the disclosures of which are incorporated herein by reference in their entirety.

In other aspects, any metallocene component of the catalyst compositions provided herein can comprise a bridged metallocene compound, e.g., with titanium, zirconium, or hafnium, such as a bridged zirconium based metallocene compound with a fluorenyl group, and with no aryl groups on the bridging group, or a bridged zirconium based metallocene compound with a cyclopentadienyl group and a fluorenyl group, and with no aryl groups on the bridging group. Such bridged metallocenes, in some aspects, can contain an alkenyl substituent (e.g., a terminal alkenyl) on the bridging group, on a cyclopentadienyl-type group (e.g., a cyclopentadienyl group or a fluorenyl group), or on the bridging group and the cyclopentadienyl-type group. In another aspect, the metallocene catalyst component can comprise a bridged zirconium or hafnium based metallocene compound with a fluorenyl group, and an aryl group on the bridging group; alternatively, a bridged zirconium or hafnium based metallocene compound with a cyclopentadienyl group and fluorenyl group, and an aryl group on the bridging group; alternatively, a bridged zirconium based metallocene compound with a fluorenyl group, and an aryl group on the bridging group; or alternatively, a bridged hafnium based metallocene compound with a fluorenyl group, and an aryl group on the bridging group. In these and other aspects, the aryl group on the bridging group can be a phenyl group. Optionally, these bridged metallocenes can contain an alkenyl substituent (e.g., a terminal alkenyl) on the bridging group, on a cyclopentadienyl-type group, or on both the bridging group and the cyclopentadienyl group. Illustrative and non-limiting examples of bridged metallocene compounds (e.g., with zirconium or hafnium) that can be employed in catalyst systems consistent with aspects of the present invention are described in U.S. Pat. Nos. 7,026,494, 7,041,617, 7,226,886, 7,312,283, 7,517,939, and 7,619,047, the disclosures of which are incorporated herein by reference in their entirety.

Various processes to produce catalyst compositions consistent with this invention are also disclosed herein. One such process can comprise:

(a) contacting a half-metallocene titanium compound having the formula:

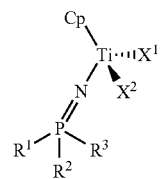

with an alkylaluminum compound having the formula $Al(R^Z)_3$ for a first period of time to form a first mixture, the first mixture comprising a bimetallic compound having the formula:

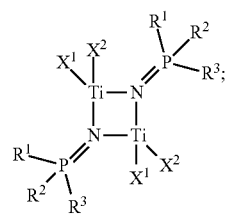

and (b) contacting the first mixture with any activator disclosed herein and optionally any co-catalyst disclosed herein for a second period of time to form the catalyst composition.

As above, in this process and formulas (A) and (B), $R^1$, $R^2$, $R^3$, $X^1$, $X^2$, Cp, and $R^Z$ are independent elements, and the process and the compounds having formula (A) or (B) can be described using any combination of $R^1$, $R^2$, $R^3$, $X^1$, $X^2$, Cp, and $R^Z$ disclosed herein. The selections for $R^1$, $R^2$, $R^3$, $X^1$, $X^2$, Cp, and $R^Z$ can be the same as those described hereinabove as it pertains to the compounds having formulas (A) and (B), and the synthesis of the bimetallic titanium compound having formula (A).

Thus, $R^1$, $R^2$, and $R^3$ independently can be H or any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein; $X^1$ and $X^2$ independently can be any halide disclosed herein, Cp can be any substituted or unsubstituted cyclopentadienyl, indenyl, or fluorenyl group disclosed herein; and each $R^Z$ independently can be any $C_1$ to $C_{10}$ alkyl group disclosed herein.

Generally, the features of the processes for producing a catalyst composition disclosed herein (e.g., the activator, the alkylaluminum compound, the half-metallocene titanium compound, the co-catalyst, the first period of time, and the second period of time, among others) are independently described herein, and these features can be combined in any combination to further describe the disclosed processes. Moreover, other process steps can be conducted before, during, and/or after any of the steps listed in the disclosed processes, unless stated otherwise. Additionally, catalyst compositions produced in accordance with the disclosed processes are within the scope of this disclosure and are encompassed herein. Unexpectedly, in these processes for producing a catalyst composition, the Cp group in formula (B) is cleaved from the titanium metal in the formation the first mixture comprising the bimetallic compound having formula (A).

Step (a) in the process for producing a catalyst composition generally can be performed as described hereinabove for the method of making a bimetallic titanium compound.

For instance, the molar ratio (Al:Ti) of the alkylaluminum compound to the half-metallocene titanium compound often can be in a range from about 0.5:1 to about 10:1, from about 0.9:1 to about 10:1, from about 1:1 to about 5:1, from about 1.1:1 to about 3:1, or from about 1.1 to about 2:1, and in some aspects, the molar ratio can be equal to about 1:1 (stoichiometric). Likewise, the contacting of the half-metallocene titanium compound having formula (B) with the alkylaluminum to form the first mixture containing the bimetallic compound can be performed at a temperature in a range from about 0° C. to about 80° C., or from about 10° C. to about 35° C., and the first period of time can be from about 15 minutes to about 48 hours, from about 30 minutes to about 36 hours, from about 1 hour to about 30 hours.

In an aspect, the first period of time can be any length of time sufficient to reduce at least a portion of the half-metallocene titanium(IV) compound to any titanium(III) species, such as a bimetallic titanium(III) compound (e.g., formula (A)). Further, the duration of the first time period can impact the amount of Ti(IV) species remaining in the mixture, where a longer time period generally can result in less residual Ti(IV) compounds. While not wishing to be bound by the following theory, it is believed that for a first period of time up to 1 hour (depending upon other reaction conditions, of course), a mixture of Ti(III) and Ti(IV) species can be present; after 1 hour, it is believed that effectively all of the Ti(IV) has reacted (assuming an excess of the alkylaluminum compound is present). Therefore, in another aspect of this invention, a suitable first period of time can be any period of time sufficient for the first mixture to be substantially free of Ti(IV) compounds, i.e., to contain less than 10 wt. % of Ti(IV) compounds. For instance, the first time period can be a period of time sufficient for the first mixture to contain less than about 8 wt. %, less than about 5 wt. %, less than about 3 wt. %, less than about 1 wt. %, less than about 0.5 wt. %, or less than about 0.1 wt. %, of Ti(IV) compounds. Accordingly, in yet another aspect of this invention, the first mixture containing the bimetallic titanium compound of formula (A) can be substantially free of Ti(IV) compounds (i.e., contain less than 10 wt. %), and in some circumstances, can contain less than about 8 wt. %, less than about 5 wt. %, less than about 3 wt. %, less than about 1 wt. %, less than about 0.5 wt. %, or less than about 0.1 wt. %, of Ti(IV) compounds. Further, the first mixture containing the bimetallic titanium compound of formula (A) can further comprise Ti(II) compounds, can further comprise additional Ti(III) compounds, or can further comprise Ti(II) compounds and additional Ti(III) compounds (other than the bimetallic compound of formula (A)).

In step (b), the first mixture is contacted with an activator and optionally a co-catalyst for a second period of time to form the catalyst composition. The second period of time is not limited to any particular period of time. Hence, the second period of time can be, for example, a time period ranging from as little as 1-10 seconds to as long as 24-48 hours, or more. The appropriate second period of time can depend upon, for example, the contacting temperature, the relative amount of the respective components, considerations for long-term storage, and the degree of mixing, among other variables. Generally, however, the second period of time can be at least about 5 sec, at least about 10 sec, at least about 30 sec, at least about 1 min, at least about 5 min, at least about 10 min, and so forth. Typical ranges for the second period of time can include, but are not limited to, from about 1 sec to about 48 hr, from about 10 sec to about 48 hr, from about 30 sec to about 24 hr, from about 30 sec to about 6 hr, from about 1 min to about 6 hr, from about 5 min to about 24 hr, or from about 10 min to about 8 hr, and the like.

Generally, the weight ratio of co-catalyst (e.g., an organoaluminum compound) to activator (e.g., activator-support) can be in a range from about 10:1 to about 1:1000. If more than one co-catalyst compound and/or more than one activator are employed, this ratio is based on the total weight of each respective component. In another aspect, the weight ratio of the co-catalyst to the activator can be in a range from about 3:1 to about 1:500, or from about 1:10 to about 1:350.

In some aspects of this invention, the weight ratio of bimetallic titanium compound to the activator (e.g., activator-support) can be in a range from about 1:1 to about 1:1,000,000. If more than one transition metal compound and/or more than activator is/are employed, this ratio is based on the total weights of the respective components. In another aspect, this weight ratio can be in a range from about 1:5 to about 1:100,000, or from about 1:10 to about 1:10,000. Yet, in another aspect, the weight ratio of the bimetallic titanium compound to the activator can be in a range from about 1:20 to about 1:1000.

Catalyst compositions of the present invention generally have a catalyst activity greater than about 20,000 grams, greater than about 50,000 grams, greater than 70,000 grams, greater than about 100,000 grams, etc., of ethylene polymer (homopolymer or copolymer, as the context requires) per gram of the bimetallic titanium compound per hour (abbreviated g/g/h). In another aspect, the catalyst activity can be greater than about 150,000, greater than about 200,000, or greater than about 300,000 g/g/h, and often can range up to 400,000-750,000 g/g/h. These activities are measured under slurry polymerization conditions, with a triisobutylaluminum co-catalyst, using isobutane as the diluent, at a polymerization temperature of 80° C. and a reactor pressure of 340 psig. Additionally, in some aspects, the activator can comprise an activator-support, such as sulfated alumina, fluorided-chlorided silica-coated alumina, or fluorided silica-coated alumina, although not limited thereto.

Activator-Supports

The present invention encompasses various catalyst compositions containing an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, 8,703,886, and 9,023,959, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also can encompass oxide materials such as silica-coated alumina, as described in U.S. Pat. No. 7,884,163 (e.g., Sasol Siral® 28, Sasol Siral® 40, etc.).

Accordingly, in one aspect, the solid oxide can comprise silica, alumina, silica-alumina, silica-coated alumina, aluminum phosphate, aluminophosphate, heteropolytungstate, titania, zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one aspect, the silica content of these solid oxides can be from about 10 to about 80%, or from about 20% to about 70%, silica by weight. In another aspect, such materials can have silica contents ranging from about 15% to about 60%, from about 20% to about 50%, or from about 25% to about 45%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion.

Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 to about 25 wt. % of the electron-withdrawing anion, based on the weight of the activator-support. In particular aspects provided herein, the activator-support can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, or from about 4 to about 10 wt. %, of the electron-withdrawing anion, based on the total weight of the activator-support.

In an aspect, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, as well as any mixture or combination thereof. In another aspect, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided-chlorided silica-coated alumina, fluorided silica-coated alumina, sulfated silica-coated alumina, and the like, as well as combinations thereof. In yet another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, etc.) are well known to those of skill in the art.

Co-Catalysts

In certain aspects directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (or non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound (e.g., a supported aluminoxane), an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Representative and non-limiting examples of organoboron/organoborate compounds include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl) ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl) borate, triphenylcarbenium tetrakis[3,5-bis(trifluoromethyl) phenyl] borate, triphenylcarbenium tetrakis (pentafluorophenyl)borate, tropylium tetrakis(p-tolyl) borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis (pentafluorophenyl) borate, lithium tetrakis (pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis (pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis (pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl) methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Polymerization Processes

Catalyst compositions of the present invention can be used to polymerize olefins to form homopolymers, copolymers, terpolymers, and the like, and are discussed herein. One such process for polymerizing olefins in the presence of a catalyst composition of the present invention can comprise contacting the catalyst composition with an olefin monomer and optionally an olefin comonomer (one or more) in a polymerization reactor system under polymerization conditions to produce an olefin polymer, wherein the catalyst composition can comprise a bimetallic titanium compound, an activator, and an optional co-catalyst. Suitable bimetallic titanium compounds, activators, and co-catalysts are discussed herein. Hence, aspects of this invention are directed to a process for polymerizing olefins in the presence of a catalyst composition, the process comprising contacting a catalyst composition with an olefin monomer and optionally an olefin comonomer (one or more) under polymerization conditions to produce an olefin polymer.

The catalyst compositions of the present invention are intended for any olefin polymerization method using various types of polymerization reactor systems and reactors. The polymerization reactor system can include any polymerization reactor capable of polymerizing olefin monomers and comonomers (one or more than one comonomer) to produce homopolymers, copolymers, terpolymers, and the like. The various types of reactors include those that can be referred to as a loop reactor, slurry reactor, gas-phase reactor, solution reactor, high pressure reactor, tubular reactor, autoclave reactor, and the like, or combinations thereof. Suitable polymerization conditions are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge. Processes can also include partial or full direct recycle of unreacted monomer, unreacted comonomer, and/or diluent.

Polymerization reactor systems of the present invention can comprise one type of reactor in a system or multiple reactors of the same or different type (e.g., a single reactor, dual reactor, more than two reactors). Production of polymers in multiple reactors can include several stages in at least two separate polymerization reactors interconnected by a transfer device making it possible to transfer the polymers resulting from the first polymerization reactor into the second reactor. The desired polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both. Accordingly, the present invention encompasses polymerization reactor systems comprising a single reactor, comprising two reactors, and comprising more than two reactors. The polymerization reactor system can comprise a slurry reactor, a gas-phase reactor, a solution reactor, in certain aspects of this invention, as well as multi-reactor combinations thereof.

According to one aspect of the invention, the polymerization reactor system can comprise at least one loop slurry reactor comprising vertical or horizontal loops. Monomer, diluent, catalyst, and comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, 6,833,415, and 8,822,608, each of which is incorporated herein by reference in its entirety.

Suitable diluents used in slurry polymerization include, but are not limited to, the monomer being polymerized and hydrocarbons that are liquids under polymerization conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used, such as can be employed in the bulk polymerization of propylene to form polypropylene homopolymers.

According to yet another aspect of this invention, the polymerization reactor system can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, 5,436,304, 7,531,606, and 7,598,327, each of which is incorporated by reference in its entirety herein.

According to still another aspect of the invention, a high pressure polymerization reactor can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect of the invention, the polymerization reactor system can comprise a solution polymerization reactor wherein the monomer (and comonomer, if used) are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the present invention can further comprise any combination of at least one raw material feed system, at least one feed system for catalyst or catalyst components, and/or at least one polymer recovery system. Suitable reactor systems for the present invention can further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 35° C. to about 280° C., for example, or from about 50° C. to about 175° C., depending upon the type of polymerization reactor(s). In some reactor systems, the polymerization temperature generally can fall within a range from about 60° C. to about 120° C., or from about 70° C. to about 100° C. Various polymerization conditions can be held substantially constant, for example, for the production of a particular grade of olefin polymer.

Suitable pressures will also vary according to the reactor and polymerization type. The pressure for liquid phase polymerizations in a loop reactor is typically less than 1000 psig (6.9 MPa). The pressure for gas phase polymerization is usually at about 200 to 500 psig (1.4 MPa to 3.4 MPa). High pressure polymerization in tubular or autoclave reactors is generally conducted at about 20,000 to 75,000 psig (138 to 517 MPa). Polymerization reactors can also be operated in a supercritical region occurring at generally higher temperatures and pressures (for instance, above 92° C. and 700 psig (4.83 MPa)). Operation above the critical point of a pressure/temperature diagram (supercritical phase) can offer advantages to the polymerization reaction process.

Aspects of this invention are directed to olefin polymerization processes conducted in the absence of added hydrogen. An olefin polymerization process of this invention can comprise contacting a catalyst composition with an olefin monomer and optionally an olefin comonomer in a polymerization reactor system under polymerization conditions to produce an olefin polymer, wherein the catalyst composition can comprise a bimetallic metallocene compound, an activator, and an optional co-catalyst, and wherein the polymerization process is conducted in the absence of added hydrogen (no hydrogen is added to the polymerization reactor system). As one of ordinary skill in the art would recognize, hydrogen can be generated in-situ by catalyst compositions in various olefin polymerization processes, and the amount generated can vary depending upon the specific catalyst composition and metallocene compound employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer in a polymerization reactor system under polymerization conditions to produce an olefin polymer, wherein the catalyst composition comprises a bimetallic titanium compound, an activator, and an optional co-catalyst, and wherein the polymerization process is conducted in the presence of added hydrogen (hydrogen is added to the polymerization reactor system). For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor system can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers (e.g., ethylene/α-olefin copolymers, ethylene homopolymers, etc.) produced by any of the polymerization processes disclosed herein. Articles of manufacture can be formed from, and/or can comprise, the polymers produced in accordance with this invention.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms, or from 3 to 10 carbon atoms, in their molecular chain.

Acyclic, cyclic, polycyclic, terminal (α), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene can also be employed as a monomer in the present invention. In an aspect, the olefin monomer can comprise a $C_2$-$C_{20}$ olefin; alternatively, a $C_2$-$C_{20}$ alpha-olefin; alternatively, a $C_2$-$C_{10}$ olefin; alternatively, a $C_2$-$C_{10}$ alpha-olefin; alternatively, the olefin monomer can comprise ethylene; or alternatively, the olefin monomer can comprise propylene.

When a copolymer (or alternatively, a terpolymer) is desired, the olefin monomer and the olefin comonomer independently can comprise, for example, a $C_2$-$C_{20}$ alpha-olefin. In some aspects, the olefin monomer can comprise ethylene or propylene, which is copolymerized with at least one comonomer (e.g., a $C_2$-$C_{20}$ alpha-olefin, a $C_3$-$C_{20}$ alpha-olefin, etc.). According to one aspect of this invention, the olefin monomer used in the polymerization process can comprise ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect of the present invention, the olefin monomer can comprise ethylene, and the comonomer can comprise a $C_3$-$C_{10}$ alpha-olefin; alternatively, the comonomer can comprise 1-butene, 1-pentene, 1-hexene, 1-octene, 1-decene, styrene, or any combination thereof alternatively, the comonomer can comprise 1-butene, 1-hexene, 1-octene, or any combination thereof alternatively, the comonomer can comprise 1-butene; alternatively, the comonomer can comprise 1-hexene; or alternatively, the comonomer can comprise 1-octene.

Generally, the amount of comonomer introduced into a polymerization reactor system to produce a copolymer can be from about 0.01 to about 50 weight percent of the comonomer based on the total weight of the monomer and comonomer. According to another aspect of the present invention, the amount of comonomer introduced into a polymerization reactor system can be from about 0.01 to about 40 weight percent comonomer based on the total weight of the monomer and comonomer. In still another aspect, the amount of comonomer introduced into a polymerization reactor system can be from about 0.1 to about 35 weight percent comonomer based on the total weight of the monomer and comonomer. Yet, in another aspect, the amount of comonomer introduced into a polymerization reactor system can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one aspect of the present invention, at least one monomer/reactant can be ethylene (or propylene), so the polymerization reaction can be a homopolymerization involving only ethylene (or propylene), or a copolymerization with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Polymers and Articles

Olefin polymers encompassed herein can include any polymer produced from any olefin monomer and comonomer(s) described herein. For example, the olefin polymer can comprise an ethylene homopolymer, a propylene homopolymer, an ethylene copolymer (e.g., ethylene/α-olefin, ethylene/1-butene, ethylene/1-hexene, ethylene/1-octene, etc.), a propylene copolymer, an ethylene terpolymer, a propylene terpolymer, and the like, including combinations thereof. In one aspect, the olefin polymer can be (or can comprise) an ethylene homopolymer, an ethylene/1-butene copolymer, an ethylene/1-hexene copolymer, or an ethylene/1-octene copolymer; or alternatively, an ethylene/1-hexene copolymer. In another aspect, the olefin polymer can be (or can comprise) a polypropylene homopolymer or a propylene-based copolymer.

If the resultant polymer produced in accordance with the present invention is, for example, an ethylene polymer, its properties can be characterized by various analytical techniques known and used in the polyolefin industry. Articles of manufacture can be formed from, and/or can comprise, the ethylene polymers of this invention, whose typical properties are provided below.

In particular aspects, and unexpectedly, the ethylene polymers disclosed herein often can have a relatively high molecular weight and high melt strength. An illustrative and non-limiting example of an ethylene polymer (e.g., an ethylene homopolymer or an ethylene/α-olefin copolymer, such as an ethylene/1-butene copolymer, an ethylene/1- hexene copolymer, or an ethylene/1-octene copolymer) consistent with aspects of this invention can have a high load melt index less than or equal to about 200 g/10 min (or from about 1 to about 100 g/10 min), and/or a density in a range from about 0.87 to about 0.96 g/cm$^3$ (or from about 0.89 to about 0.93 g/cm$^3$), and/or a Mw in a range from about 50,000 to about 750,000 g/mol (or from about 70,000 to about 500,000 g/mol), and/or a ratio of Mw/Mn in a range from about 2 to about 18 (or from about 3 to about 12).

These illustrative and non-limiting examples of ethylene polymers consistent with the present invention also can have any of the polymer properties listed below and in any combination.

The densities of ethylene polymers produced using the catalyst systems and polymerization processes described herein often range from about 0.87 to about 0.96 g/cm$^3$. In one aspect of this invention, the density of the ethylene polymer can be in a range from about 0.93 to about 0.96, or from about 0.87 to about 0.94 g/cm$^3$. Yet, in another aspect, the density can be in a range from about 0.88 to about 0.93 g/cm$^3$, such as, for example, from about 0.89 to about 0.93 g/cm$^3$, from about 0.895 to about 0.925 g/cm$^3$, or from about 0.90 to about 0.92 g/cm$^3$.

Suitable non-limiting ranges for the high load melt index (HLMI) of the ethylene polymer can include a HLMI less than or equal to about 200, less than or equal to about 100, less than or equal to about 50, or less than or equal to about 25 g/10 min. In some aspects, the ethylene polymer can have a HLMI in a range from about 1 to about 200, from about 1 to about 100, from about 1 to about 50, from about 5 to about 50, or from about 5 to about 25 g/10 min.

The ethylene polymer, in some aspects, can have a relatively broad molecular weight distribution, with a ratio of Mw/Mn in a range from about 2 to about 18, for example, from about 2.5 to about 15, from about 3 to about 15, or from about 3 to about 12. Generally, the ethylene polymer can have a number-average molecular weight (Mn) in a range from about 10,000 to about 150,000, from about 10,000 to about 100,000, from about 12,000 to about 100,000, or from about 14,000 to about 90,000 g/mol. Additionally or alternatively, the ethylene polymer can have a weight-average molecular weight (Mw) in a range from about 50,000 to about 750,000, from about 60,000 to about 600,000, from about 70,000 to about 500,000, or from about 100,000 to about 500,000 g/mol. Other suitable ranges for Mw can include, but are not limited to, from about 100,000 to about 750,000, from about 140,000 to about 500,000, or from about 150,000 to about to about 450,000 g/mol.

The ethylene polymer, in some aspects, can have ratio of Mz/Mw in a range from about 1.8 to about 10, for example, from about 2 to about 10, from about 2 to about 9, or from about 2 to about 8. Generally, the ethylene polymer can have a Z-average molecular weight (Mz) in a range from about 300,000 to about 2,500,000, from about 300,000 to about 1,500,000, from about 500,000 to about 1,500,000, or from about 500,000 to about 1,000,000 g/mol. Other suitable ranges for Mz can include, but are not limited to, from about 600,000 to about 1,250,000, from about 750,000 to about 1,000,000, or from about 1,000,000 to about 1,500,000 g/mol. Additionally or alternatively, the ethylene polymer can have a peak molecular weight (Mp) in a range from about 50,000 to about 500,000, from about 60,000 to about 400,000, from about 50,000 to about 250,000, from about 100,000 to about 250,000 or from about 200,000 to about 500,000 g/mol. In these and other aspects, the ethylene polymer can have a unimodal molecular weight distribution.

Polymers of ethylene, whether homopolymers, copolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual— Process, Materials, Properties*, TAPPI Press, 1992; the disclosures of which are incorporated herein by reference in their entirety.

Also contemplated herein is a method for forming or preparing an article of manufacture that comprises a polymer produced by any of the polymerization processes disclosed herein. For instance, the method can comprise (i) contacting a catalyst composition with an olefin monomer and an optional olefin comonomer under polymerization conditions in a polymerization reactor system to produce an olefin polymer, wherein the catalyst composition can comprise a bimetallic titanium compound (e.g., having formula (A)), an activator (e.g., an activator-support comprising a solid oxide treated with an electron-withdrawing anion), and an optional co-catalyst (e.g., an organoaluminum compound); and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Melt index (MI, g/10 min) was determined in accordance with ASTM D1238 at 190° C. with a 2,160 gram weight, and high load melt index (HLMI, g/10 min) was determined in accordance with ASTM D1238 at 190° C. with a 21,600 gram weight.

Molecular weights and molecular weight distributions were obtained using a PL-GPC 220 (Polymer Labs, an Agilent Company) system equipped with a IR4 detector (Polymer Char, Spain) and three Styragel HMW-6E GPC columns (Waters, MA) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation was conducted at 150° C. for nominally 4 hr with occasional and gentle agitation, before the solutions were transferred to sample vials for injection. An injection volume of about 200 µL was used. The integral calibration method was used to deduce molecular weights and molecular weight distributions using a Chevron Phillips Chemical Company's HDPE polyethylene resin, MAR-LEX® BHB5003, as the standard. The integral table of the standard was pre-determined in a separate experiment with SEC-MALS. Mn is the number-average molecular weight, Mw is the weight-average molecular weight, and Mz is the z-average molecular weight.

X-ray crystal structures were determined from single crystal diffraction data obtained on a Bruker ULTRA diffractometer with Mo—K rotating-anode alpha radiation source and a APEXII CCD area detector.

Fluorided silica-coated alumina activator-supports were prepared as follows. Bohemite was obtained from W.R. Grace & Company under the designation "Alumina A" and having a surface area of 300 m²/g, a pore volume of 1.3 mL/g, and an average particle size of 100 microns. The alumina was first calcined in dry air at about 600° C. for approximately 6 hours, cooled to ambient temperature, and then contacted with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (FSCA) was collected and stored under dry nitrogen, and was used without exposure to the atmosphere.

Example A

Synthesis of a Bimetallic Titanium Compound Using a Pre-Reduction Step.

A nitrogen-filled MBraun LabMaster DP glovebox was utilized for the storage and manipulation of all moisture- and oxygen-sensitive compounds and reagents. Reactions were carried out in a Chemglass AirFree® vacuum manifold utilizing swivel frit assemblies under nitrogen. Anhydrous benzene, toluene and pentane were purchased from Sigma-Aldrich and stored over AZ300 desiccant. Benzene-d6 was purchased from Cambridge Isotope Laboratories and dried and stored over A201 desiccant prior to use.

The synthesis scheme for the bimetallic titanium compound in Example A, using a pre-reducing step, is shown below (t-Bu=tert-butyl; Cp=unsubstituted indenyl).

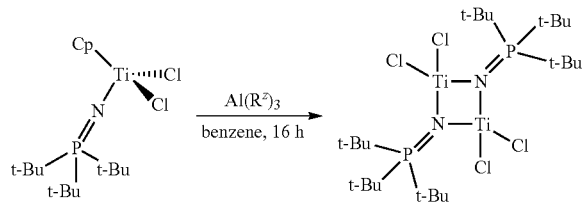

In Example A, a 1 M solution of triisobutylaluminum (2.22 mL, 2.22 mmol) was added dropwise to a room temperature solution of [(Ind)TiCl₂(N=P(t-Bu)₃)] (1 g, 2.22 mmol) in benzene (50 mL) and stirred at room temperature. The color of the solution gradually changed after approximately 10 minutes from light yellow-orange to a green-black. After stirring for 16 hours, the benzene was removed in vacuo and pentane (ca. 30 mL) was added, followed by sonication and filtration to yield a clear, emerald-green solution. Removal of pentane in vacuo yielded 1.154 g of a dark green oil. X-ray quality crystals were obtained by layering a saturated toluene solution with pentane at −30° C.

The crystal structure for the bimetallic titanium compound of Example A is shown in FIG. 1. Surprisingly, as shown in the above reaction scheme, the cyclopentadienyl-type group (in this case, an indenyl group) was cleaved from the titanium to form the bimetallic titanium (III) compound.

Examples 1-17

Polymerization Experiments with Bimetallic Titanium Compounds.

The general procedure for the polymerization experiments was performed as follows, either with or without a pre-reduction step. The polymerization experiments were conducted in a one-gallon stainless steel reactor, and isobutane (1.2 L) was used in all experiments. Solutions of the half-metallocene titanium compound were prepared at about 1 mg/mL in toluene. In experiments where a pre-reduction step was employed, in a manner similar to Example A, the half-metallocene titanium solution was combined with an alkylaluminum solution (1 M in hexanes) at a 1:1-5:1 molar ratio of Al:Ti for 16-24 hours to form a mixture containing the bimetallic titanium compound.

The activator-support (FSCA) or borane (tris(pentafluorophenyl)boron; 1:1 molar ratio of B:Ti), an additional amount of an organoaluminum compound (same compound used in the reduction step; 150 ppm by weight of the organoaluminum compound based on the weight of isobutane), and the mixture containing the bimetallic titanium compound (or the solution of the half-metallocene compound) were added in that order through a charge port while slowly venting isobutane vapor. An exception was Example 11, where the FSCA, alkylaluminum, and the titanium half-metallocene titanium solution were contacted in that order to form the catalyst system. The charge port was closed and isobutane was added. The contents of the reactor were stirred and heated to the desired polymerization temperature of 80° C. Ethylene, 1-hexene (10 grams), and hydrogen (ranging from 125 to 250 ppm by weight, based on ethylene) were then introduced into the reactor. Ethylene and hydrogen were fed on demand to maintain the target pressure of 340 psig for 20 minutes (Examples 9 and 10 were conducted for 30 and 60 minutes, respectively). The reactor was maintained at 80° C. throughout the run by an automated heating-cooling system. After venting of the reactor, purging, and cooling, the resulting polymer product was dried under reduced pressure.

The structures of half-metallocene titanium compounds MET-1 and MET-2 are shown below (MET-3 was similar to MET-2, but with a pentamethyl-cyclopentadienyl group):

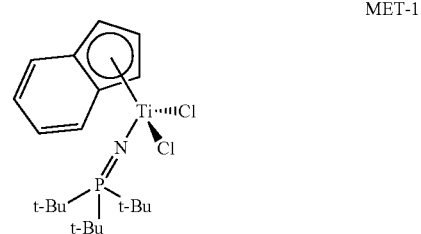

MET-1

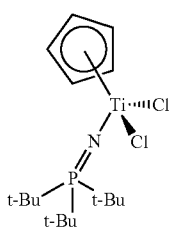

MET-2

As shown in Table I, different activators (FSCA or borane), alkylaluminum reducing agents (TIBA=triisobutylaluminum, TEA=triethylaluminum, TMA=trimethylaluminum, and TOA=trioctylaluminum), and half-metallocene titanium compounds were employed in polymerization experiments, performed as described above, either with a pre-reduction step (to form a bimetallic titanium compound) or without a pre-reduction step (half-metallocene titanium compound). The catalyst activity in Table I is listed in grams of polymer per gram of titanium half-metallocene compound per hour. Unexpectedly, the use of DEAC (diethylaluminum chloride) in Example 7 resulted in a catalyst system with no polymerization activity.

Figure 10:
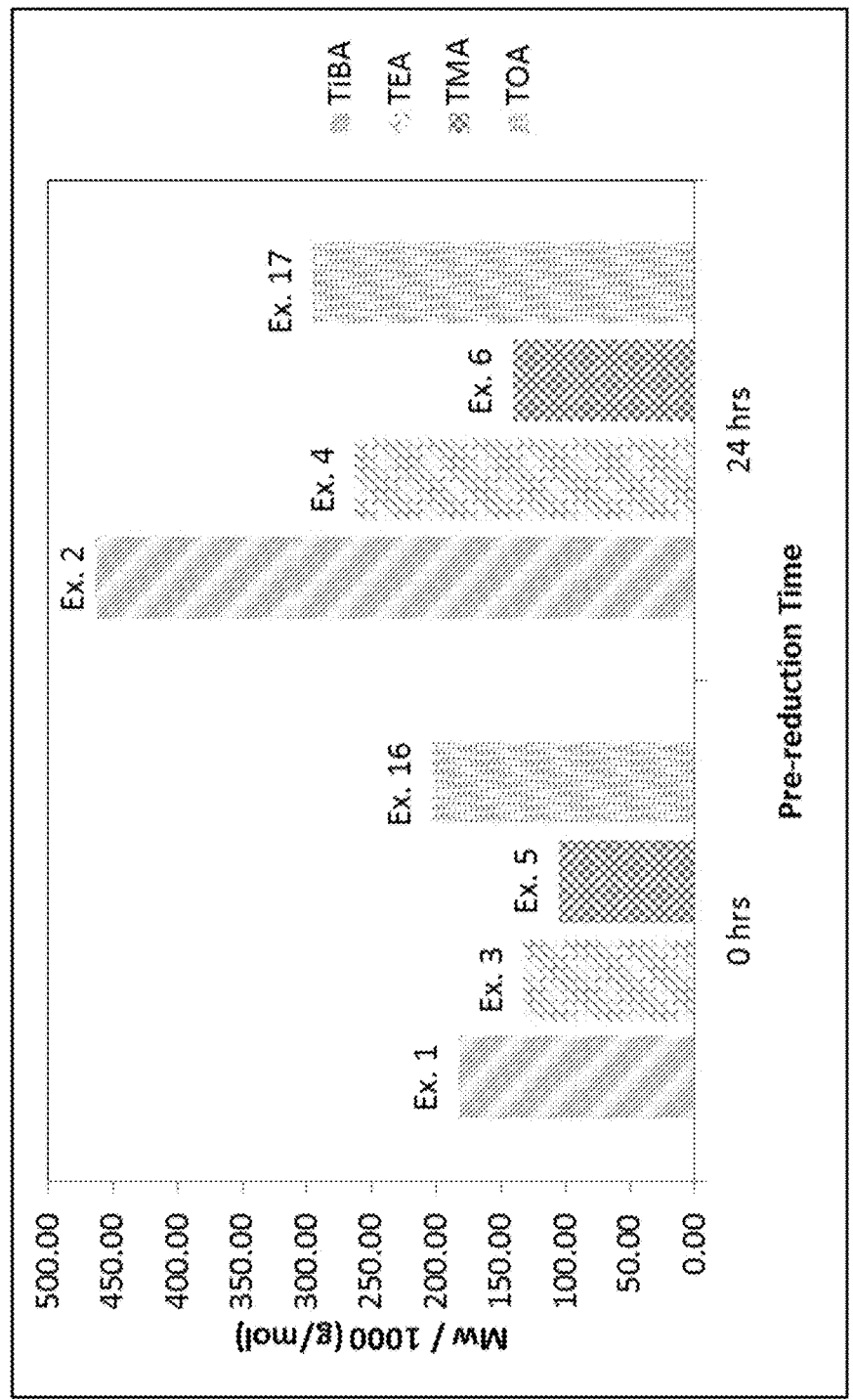
FIG. 10 is a bar chart illustrating the impact of pre-reduction time on the Mw of polymers produced using different alkylaluminum compounds.
Figure 11:
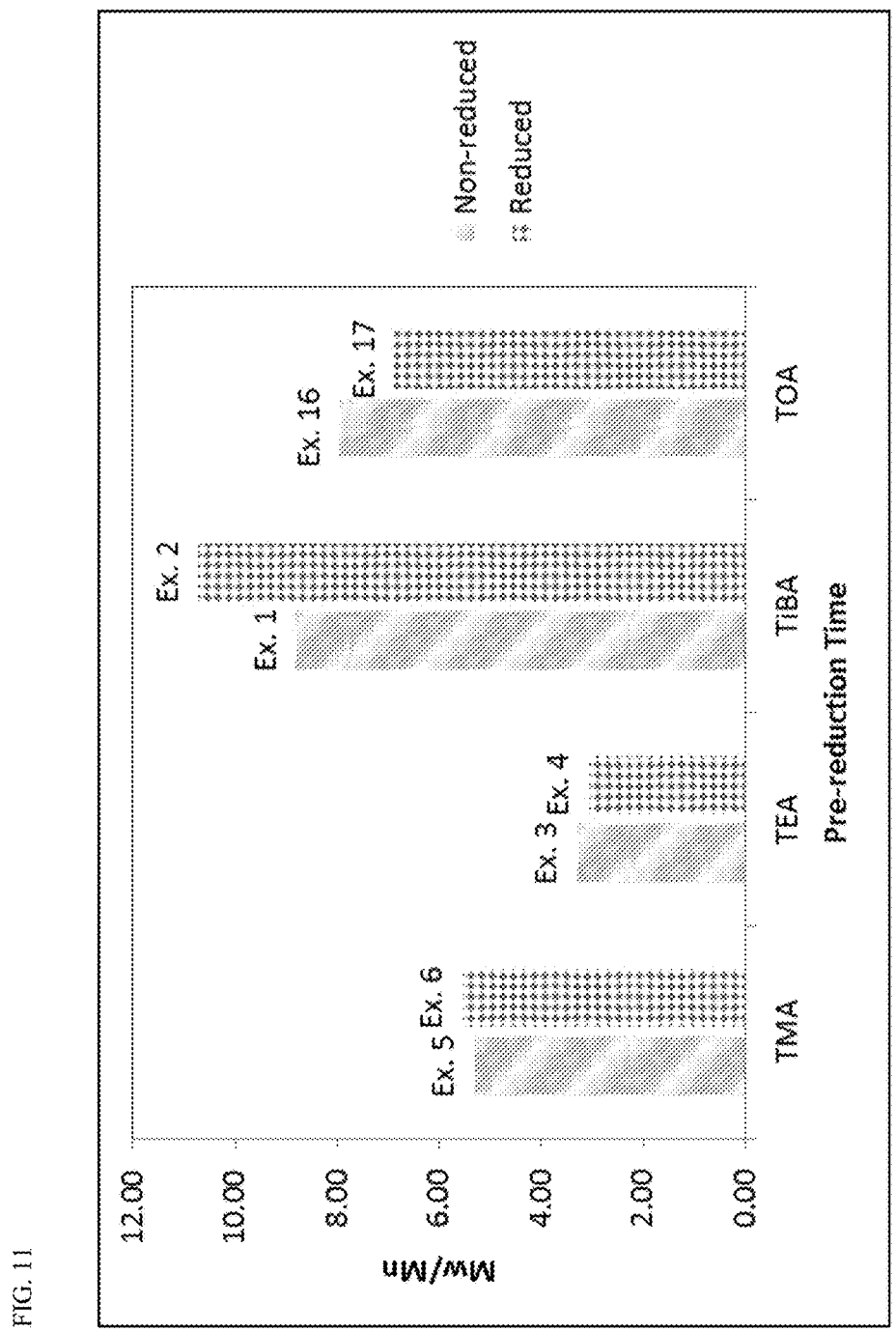
FIG. 11 is a bar chart illustrating the impact of pre-reduction time on the ratio of Mw/Mn of polymers produced using different alkylaluminum compounds.

Table II summarizes certain polymer properties for the polymers produced in Examples 1-17, FIGS. 2-9 illustrate the molecular weight distributions (amount of polymer versus the logarithm of molecular weight) for the some of the polymers shown in Table II, and FIGS. 10-11 are bar charts that demonstrate the impact of the pre-reduction step on the Mw and the ratio of Mw/Mn of certain polymers produced using different alkylaluminum compounds.

Unexpectedly, the tables and figures demonstrate that ethylene polymers produced using the inventive catalyst composition—containing a bimetallic titanium compound formed in a pre-reduction step—had much higher molecular weights than the same catalyst system without the pre-reduction step (i.e., using the half-metallocene titanium compound). For instance, each of Examples 1-2, Examples 3-4, Examples 5-6, Examples 12-13, and Examples 16-17 demonstrate the higher Mn, higher Mw, higher Mz, and lower HLMI of polymers produced using the bimetallic titanium compound, as compared to the half-metallocene titanium compound. FIG. 10 summarizes some of these results for four different alkylaluminum compounds.

The tables and figures also demonstrate a surprising impact of the selection of alkylaluminum compound on the molecular weight properties of the polymer produced. FIG. 10 illustrates the impact of the alkylaluminum compound on the Mw of the polymer produced, with or without a pre-reduction step. Likewise, FIG. 11 illustrates the impact of the alkylaluminum compound on ratio of Mw/Mn (a measure of the breadth of the molecular weight distribution) of the polymer produced, with or without a pre-reduction step. Using TEA resulted in the narrowest molecular weight distribution (Mw/Mn ~3), while TMA gave a broader molecular weight distribution (Mw/Mn ~5), and TOA resulted in an even broader molecular weight distribution (Mw/Mn ~6-8), and TIBA gave the broadest molecular weight distribution (Mw/Mn ~8-11).

Thus, it was unexpectedly found—for the catalyst compositions disclosed herein and their use in olefin polymerizations—that molecular weight properties can be tailored based on the selection of the alkylaluminum compound used in the pre-reduction step.

TABLE I

Examples 1-17-Polymerization Conditions

| Ex. | Half-Metallocene | Pre-reduction | Activator | Activator (g) | $Al(R^Z)_3$ | $H_2$ (ppm) | Ti activity |
|---|---|---|---|---|---|---|---|
| 1 | MET-1 | No | FSCA | 0.101 | TIBA | 125 | 366,000 |
| 2 | MET-1 | Yes | FSCA | 0.104 | TIBA | 125 | 348,000 |
| 3 | MET-1 | No | FSCA | 0.094 | TEA | 125 | 279,000 |
| 4 | MET-1 | Yes | FSCA | 0.111 | TEA | 125 | 255,000 |
| 5 | MET-1 | No | FSCA | 0.105 | TMA | 125 | 177,000 |
| 6 | MET-1 | Yes | FSCA | 0.113 | TMA | 125 | 186,000 |
| 7 | MET-1 | Yes | FSCA | 0.108 | DEAC | 125 | 0 |
| 8 | MET-1 | No | Borane | N/A | TIBA | 125 | 204,000 |
| 9 | MET-1 | No | Borane | N/A | TIBA | 250 | 83,000 |
| 10 | MET-1 | Yes | Borane | N/A | TIBA | 250 | 192,000 |
| 11 | MET-1 | — | FSCA | 0.110 | TEA | 125 | 24,000 |
| 12 | MET-2 | No | FSCA | 0.106 | TEA | 150 | 78,000 |
| 13 | MET-2 | Yes | FSCA | 0.105 | TEA | 150 | 72,000 |
| 14 | MET-3 | No | FSCA | 0.095 | TEA | 125 | 378,000 |
| 15 | MET-3 | Yes | FSCA | 0.091 | TEA | 125 | 354,000 |
| 16 | MET-1 | No | FSCA | 0.105 | TOA | 125 | 384,000 |
| 17 | MET-1 | Yes | FSCA | 0.100 | TOA | 125 | 309,000 |

TABLE II

Examples 1-17-Polymer Properties

| Ex. | MI (g/10 min) | HLMI (g/10 min) | Mn/1000 (g/mol) | Mw/1000 (g/mol) | Mz/1000 (g/mol) | Mw/Mn |
|---|---|---|---|---|---|---|
| 1 | 0.9 | 41.9 | 20.7 | 181.9 | 960 | 8.79 |
| 2 | 0 | 0.3 | 43.1 | 461.9 | 1399 | 10.71 |
| 3 | 1.0 | 26.5 | 40.1 | 132.1 | 314 | 3.29 |
| 4 | 0 | 1.3 | 85.8 | 261.9 | 547 | 3.05 |
| 5 | 5.3 | 169.6 | 19.8 | 104.9 | 606 | 5.30 |
| 6 | 2.2 | 78.6 | 25.4 | 140.2 | 669 | 5.53 |

TABLE II-continued

Examples 1-17-Polymer Properties

| Ex. | MI (g/10 min) | HLMI (g/10 min) | Mn/1000 (g/mol) | Mw/1000 (g/mol) | Mz/1000 (g/mol) | Mw/Mn |
|---|---|---|---|---|---|---|
| 7 | — | — | — | — | — | — |
| 8 | 0 | 0 | 57.3 | 700.2 | 1947 | 12.23 |
| 9 | 0 | 1.8 | 26.8 | 390.6 | 2181 | 14.56 |
| 10 | 0.5 | 54.1 | 20.5 | 175.8 | 1119 | 8.58 |
| 11 | — | — | — | — | — | — |
| 12 | 0 | 0.4 | 84.1 | 389.3 | 1127 | 4.63 |
| 13 | 0 | 0.1 | 139.4 | 657.1 | 1871 | 4.72 |
| 14 | 4.0 | 104.4 | 22.6 | 103.1 | 277 | 4.56 |
| 15 | 6.4 | 161.2 | 18.9 | 86.2 | 227 | 4.57 |
| 16 | 0.2 | 13.3 | 25.5 | 202.6 | 752 | 7.94 |
| 17 | 0 | 2.4 | 42.9 | 294.8 | 1092 | 6.86 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A method of making a bimetallic compound having the formula:

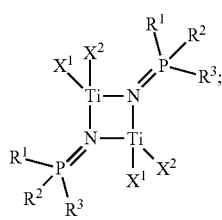

(A)

the method comprising:
contacting a half-metallocene titanium compound having the formula:

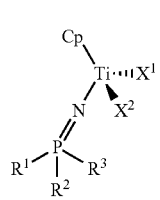

(B)

with an alkylaluminum compound having the formula $Al(R^Z)_3$ to form a mixture comprising the bimetallic compound having formula (A); wherein:

$X^1$ and $X^2$ independently are any halide disclosed herein;

$R^1$, $R^2$, and $R^3$ independently are H or any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein;

Cp is any substituted or unsubstituted cyclopentadienyl, indenyl, or fluorenyl group disclosed herein; and each $R^Z$ independently is any $C_1$ to $C_{10}$ alkyl group disclosed herein.

Aspect 2. The method defined in aspect 1, wherein Cp is unsubstituted.

Aspect 3. The method defined in aspect 1, wherein Cp is substituted with any suitable substituent, any suitable number of substituents, and at any suitable position(s) that conforms to the rules of chemical valence.

Aspect 4. The method defined in aspect 1, wherein Cp is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 5. The method defined in aspect 1, wherein Cp is substituted, and each substituent independently is H or a $C_1$ to $C_{12}$ hydrocarbyl group.

Aspect 6. The method defined in aspect 1, wherein Cp is an unsubstituted indenyl group.

Aspect 7. The method defined in any one of aspects 1-6, wherein each $R^Z$ independently is a $C_1$ to $C_8$ alkyl group, or a $C_1$ to $C_4$ alkyl group.

Aspect 8. The method defined in any one of aspects 1-6, wherein each $R^Z$ independently is a methyl group, an ethyl group, a propyl group, a n-butyl group, an isobutyl group, or a hexyl group.

Aspect 9. The method defined in any one of aspects 1-6, wherein the alkylaluminum compound comprises any alkylaluminum compound disclosed herein, e.g., trimethylaluminum, triethylaluminum, triisobutylaluminum, etc., or combinations thereof.

Aspect 10. The method defined in any one of aspects 1-9, wherein the half-metallocene titanium compound and the alkylaluminum compound are contacted for and/or the mixture comprising the bimetallic compound is formed in any suitable period of time or a period of time in any range disclosed herein, from about 15 min to about 48 hr, from about 30 min to about 36 hr, from about 1 hr to about 30 hr, etc.

Aspect 11. The method defined in any one of aspects 1-10, wherein the half-metallocene titanium compound and the alkylaluminum compound are contacted for and/or the mixture comprising the bimetallic compound is formed in a time period sufficient for the mixture to be substantially free of Ti(IV) compounds, e.g., less than 10 wt. %, less than 5 wt. %, less than 1 wt. %, etc.

Aspect 12. The method defined in any one of aspects 1-11, wherein the half-metallocene titanium compound and the alkylaluminum compound are contacted at and/or the mixture comprising the bimetallic compound is formed at any suitable temperature or at a temperature in any range disclosed herein, from about 0 to about 80° C., from about 10 to about 35° C., etc.

Aspect 13. The method defined in any one of aspects 1-12, wherein the molar ratio (Al:Ti) of the alkylaluminum compound to the half-metallocene titanium compound is any suitable molar ratio or a molar ratio in any range disclosed herein, e.g., from about 0.9:1 to about 10:1, from about 1:1 to about 5:1, from about 1.1:1 to about 2:1, equal to about 1:1, etc.

Aspect 14. The method defined in any one of aspects 1-13, wherein the mixture is substantially free of Ti(IV) compounds, e.g., less than 10 wt. %, less than 5 wt. %, less than 1 wt. %, etc.

Aspect 15. The method defined in any one of aspects 1-14, wherein the mixture further comprises Ti(II) compounds and/or additional Ti(III) compounds.

Aspect 16. A bimetallic compound prepared by the method defined in any one of aspects 1-15.

Aspect 17. A bimetallic titanium compound having the formula:

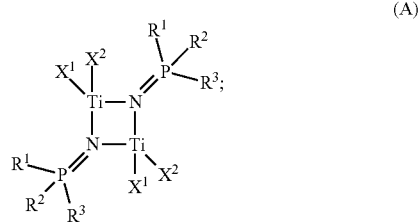

(A)

wherein:

$X^1$ and $X^2$ independently are any halide disclosed herein; and $R^1$, $R^2$, and $R^3$ independently are H or any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein.

Aspect 18. The method or compound defined in any one of aspects 1-17, wherein $X^1$ and $X^2$ are Cl.

Aspect 19. The method or compound defined in any one of aspects 1-18, wherein $R^1$, $R^2$, and $R^3$ independently are H or a $C_1$ to $C_{18}$ hydrocarbyl group.

Aspect 20. The method or compound defined in any one of aspects 1-18, wherein $R^1$, $R^2$, and $R^3$ independently are H, Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a 2,6-diisopropylphenyl group, a tolyl group, a benzyl group, a naphthyl group, a trimethylsilyl group, a triisopropylsilyl group, a triphenylsilyl group, or an allyldimethylsilyl group.

Aspect 21. The method or compound defined in any one of aspects 1-20, wherein at least one of $R^1$, $R^2$, and $R^3$ is a $C_3$ to $C_{12}$ alkenyl group.

Aspect 22. The method or compound defined in any one of aspects 1-18, wherein $R^1$, $R^2$, and $R^3$ independently are a $C_1$ to $C_8$ alkyl group.

Aspect 23. A process for producing a catalyst composition, the process comprising:

(a) contacting a half-metallocene titanium compound having the formula:

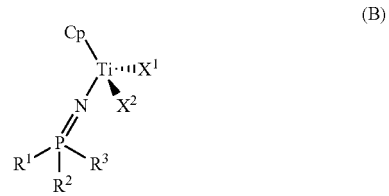

(B)

with an alkylaluminum compound having the formula $Al(R^Z)_3$ for a first period of time to form a first mixture, the first mixture comprising a bimetallic compound having the formula:

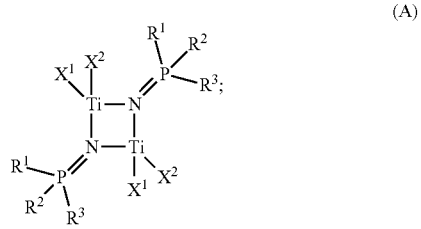

(A)

and (b) contacting the first mixture with any activator disclosed herein and optionally any co-catalyst disclosed herein for a second period of time to form the catalyst composition; wherein:

$X^1$ and $X^2$ independently are any halide disclosed herein;

$R^1$, $R^2$, and $R^3$ independently are H or any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein;

Cp is any substituted or unsubstituted cyclopentadienyl, indenyl, or fluorenyl group disclosed herein; and each $R^Z$ independently is any $C_1$ to $C_{10}$ alkyl group disclosed herein.

Aspect 24. The process defined in aspect 23, wherein Cp is unsubstituted.

Aspect 25. The process defined in aspect 23, wherein Cp is substituted with any suitable substituent, any suitable number of substituents, and at any suitable position(s) that conforms to the rules of chemical valence.

Aspect 26. The process defined in aspect 23, wherein Cp is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 27. The process defined in aspect 23, wherein Cp is substituted, and each substituent independently is H or a $C_1$ to $C_{12}$ hydrocarbyl group.

Aspect 28. The process defined in aspect 23, wherein Cp is an unsubstituted indenyl group.

Aspect 29. The process defined in any one of aspects 23-28, wherein each $R^Z$ independently is a $C_1$ to $C_8$ alkyl group, or a $C_1$ to $C_4$ alkyl group.

Aspect 30. The process defined in any one of aspects 23-28, wherein each $R^Z$ independently is a methyl group, an ethyl group, a propyl group, a n-butyl group, an isobutyl group, or a hexyl group.

Aspect 31. The process defined in any one of aspects 23-28, wherein the alkylaluminum compound comprises any alkylaluminum compound disclosed herein, e.g., trimethylaluminum, triethylaluminum, triisobutylaluminum, etc., or combinations thereof.

Aspect 32. The process defined in any one of aspects 23-31, wherein the first period of time is any suitable time period or in any range of first time periods disclosed herein, e.g., from about 15 min to about 48 hr, from about 30 min to about 36 hr, from about 1 hr to about 30 hr, etc.

Aspect 33. The process defined in any one of aspects 23-32, wherein first period of time is a time period sufficient for the first mixture to be substantially free of Ti(IV) compounds, e.g., less than 10 wt. %, less than 5 wt. %, less than 1 wt. %, etc.

Aspect 34. The process defined in any one of aspects 23-33, wherein step (a) is conducted at any suitable temperature or at a temperature in any range disclosed herein, from about 0 to about 80° C., from about 10 to about 35° C., etc.

Aspect 35. The process defined in any one of aspects 23-34, wherein the molar ratio (Al:Ti) of the alkylaluminum compound to the half-metallocene titanium compound is any suitable molar ratio or a molar ratio in any range disclosed herein, e.g., from about 0.9:1 to about 10:1, from about 1:1 to about 5:1, from about 1.1:1 to about 2:1, equal to about 1:1, etc.

Aspect 36. The process defined in any one of aspects 23-35, wherein the first mixture is substantially free of Ti(IV) compounds, e.g., less than 10 wt. %, less than 5 wt. %, less than 1 wt. %, etc.

Aspect 37. The process defined in any one of aspects 23-36, wherein the first mixture further comprises Ti(II) compounds and/or additional Ti(III) compounds.

Aspect 38. The process defined in any one of aspects 23-37, wherein the second period of time is any suitable time period or in any range of second time periods disclosed herein, e.g., from about 1 sec to about 48 hr, from about 1 min to about 6 hr, at least about 5 min, at least about 10 min, etc.

Aspect 39. A catalyst composition produced by the process defined in any one of aspects 23-38.

Aspect 40. A catalyst composition comprising a bimetallic titanium compound, any activator disclosed herein, and optionally, any co-catalyst disclosed herein, wherein the bimetallic titanium compound has the formula:

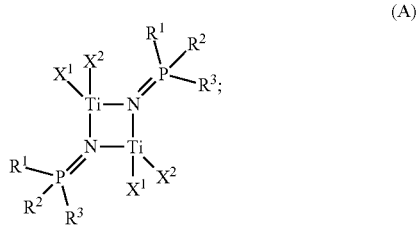

(A)

wherein:

$X^1$ and $X^2$ independently are any halide disclosed herein; and $R^1$, $R^2$, and $R^3$ independently are H or any halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group disclosed herein.

Aspect 41. The process or composition defined in any one of aspects 23-40, wherein $X^1$ and $X^2$ are Cl.

Aspect 42. The process or composition defined in any one of aspects 23-41, wherein $R^1$, $R^2$, and $R^3$ independently are H or a $C_1$ to $C_{18}$ hydrocarbyl group.

Aspect 43. The process or composition defined in any one of aspects 23-41, wherein $R^1$, $R^2$, and $R^3$ independently are H, Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a 2,6-diisopropylphenyl group, a tolyl group, a benzyl group, a naphthyl group, a trimethylsilyl group, a triisopropylsilyl group, a triphenylsilyl group, or an allyldimethylsilyl group.

Aspect 44. The process or composition defined in any one of aspects 23-43, wherein at least one of $R^1$, $R^2$, and $R^3$ is a $C_3$ to $C_{12}$ alkenyl group.

Aspect 45. The process or composition defined in any one of aspects 23-41, wherein $R^1$, $R^2$, and $R^3$ independently are a $C_1$ to $C_8$ alkyl group.

Aspect 46. The process or composition defined in any one of aspects 23-45, wherein the activator comprises an aluminoxane compound, an organoboron or organoborate compound, an ionizing ionic compound, or any combination thereof.

Aspect 47. The process or composition defined in any one of aspects 23-45, wherein the activator comprises an aluminoxane compound.

Aspect 48. The process or composition defined in any one of aspects 23-45, wherein the activator comprises an organoboron or organoborate compound.

Aspect 49. The process or composition defined in any one of aspects 23-45, wherein the activator comprises an ionizing ionic compound.

Aspect 50. The process or composition defined in any one of aspects 23-45, wherein the activator comprises an activator-support, the activator-support comprising any solid oxide treated with any electron-withdrawing anion disclosed herein.

Aspect 51. The process or composition defined in aspect 50, wherein the solid oxide comprises any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Aspect 52. The process or composition defined in aspect 50, wherein the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, or any combination thereof.

Aspect 53. The process or composition defined in aspect 50, wherein the activator-support comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Aspect 54. The process or composition defined in aspect 50, wherein the activator-support comprises a fluorided solid oxide, a sulfated solid oxide, or any combination thereof.

Aspect 55. The process or composition defined in any one of aspects 23-54, wherein the catalyst composition comprises a co-catalyst, e.g., any co-catalyst disclosed herein.

Aspect 56. The process or composition defined in any one of aspects 23-55, wherein the co-catalyst comprises an organoaluminum compound, an organozinc compound, an organomagnesium compound, an organolithium compound, or any combination thereof.

Aspect 57. The process or composition defined in any one of aspects 23-56, wherein the co-catalyst comprises an organoaluminum compound, e.g., trimethylaluminum, triethylaluminum, triisobutylaluminum, etc., or combinations thereof.

Aspect 58. The process or composition defined in any one of aspects 50-55, wherein the co-catalyst comprises an aluminoxane compound, an organoboron or organoborate compound, an ionizing ionic compound, an organoaluminum compound, an organozinc compound, an organomagnesium compound, an organolithium compound, or any combination thereof.

Aspect 59. The process or composition defined in any one of aspects 23-45 and 50-57, wherein the catalyst composition is substantially free of aluminoxane compounds, organoboron or organoborate compounds, ionizing ionic compounds, or combinations thereof.

Aspect 60. The process or composition defined in any one of aspects 23-59, wherein a catalyst activity of the catalyst composition is in any range disclosed herein, e.g., greater than about 20,000 grams, greater than about 50,000 grams, greater than about 100,000 grams, etc., of ethylene polymer per gram of the bimetallic titanium compound per hour, under slurry polymerization conditions, with a triisobutylaluminum co-catalyst, using isobutane as a diluent, and with a polymerization temperature of 80° C. and a reactor pressure of 340 psig.

Aspect 61. The process or composition defined in any one of aspects 23-60, wherein the catalyst composition further comprises any suitable metallocene compound or any metallocene compound disclosed herein.

Aspect 62. An olefin polymerization process, the process comprising contacting the catalyst composition defined in any one of aspects 39-61 with an olefin monomer and an optional olefin comonomer in a polymerization reactor system under polymerization conditions to produce an olefin polymer.

Aspect 63. The process defined in aspect 62, wherein the olefin monomer comprises any olefin monomer disclosed herein, e.g., any $C_2$-$C_{20}$ olefin.

Aspect 64. The process defined in aspect 62 or 63, wherein the olefin monomer and the optional olefin comonomer independently comprise a $C_2$-$C_{20}$ alpha-olefin.

Aspect 65. The process defined in any one of aspects 62-64, wherein the olefin monomer comprises ethylene.

Aspect 66. The process defined in any one of aspects 62-65, wherein the catalyst composition is contacted with ethylene and an olefin comonomer comprising a $C_3$-$C_{10}$ alpha-olefin.

Aspect 67. The process defined in any one of aspects 62-66, wherein the catalyst composition is contacted with ethylene and an olefin comonomer comprising 1-butene, 1-hexene, 1-octene, or a mixture thereof.

Aspect 68. The process defined in any one of aspects 62-64, wherein the olefin monomer comprises propylene.

Aspect 69. The process defined in any one of aspects 62-68, wherein the polymerization reactor system comprises a batch reactor, a slurry reactor, a gas-phase reactor, a solution reactor, a high pressure reactor, a tubular reactor, an autoclave reactor, or a combination thereof.

Aspect 70. The process defined in any one of aspects 62-69, wherein the polymerization reactor system comprises a slurry reactor, a gas-phase reactor, a solution reactor, or a combination thereof.

Aspect 71. The process defined in any one of aspects 62-70, wherein the polymerization reactor system comprises a loop slurry reactor.

Aspect 72. The process defined in any one of aspects 62-71, wherein the polymerization reactor system comprises a single reactor.

Aspect 73. The process defined in any one of aspects 62-71, wherein the polymerization reactor system comprises 2 reactors.

Aspect 74. The process defined in any one of aspects 62-71, wherein the polymerization reactor system comprises more than 2 reactors.

Aspect 75. The process defined in any one of aspects 62-74, wherein the olefin polymer comprises any olefin polymer disclosed herein.

Aspect 76. The process defined in any one of aspects 62-75, wherein the olefin polymer comprises an ethylene homopolymer, an ethylene/1-butene copolymer, an ethylene/1-hexene copolymer, or an ethylene/1-octene copolymer.

Aspect 77. The process defined in any one of aspects 62-76, wherein the olefin polymer comprises an ethylene/1-hexene copolymer.

Aspect 78. The process defined in any one of aspects 62-75, wherein the olefin polymer comprises a polypropylene homopolymer or a propylene-based copolymer.

Aspect 79. The process defined in any one of aspects 62-78, wherein the polymerization conditions comprise a polymerization reaction temperature in a range from about 60° C. to about 120° C. and a reaction pressure in a range from about 200 to about 1000 psig (about 1.4 to about 6.9 MPa).

Aspect 80. The process defined in any one of aspects 62-79, wherein the polymerization conditions are substantially constant, e.g., for a particular polymer grade.

Aspect 81. The process defined in any one of aspects 62-80, wherein no hydrogen is added to the polymerization reactor system.

Aspect 82. The process defined in any one of aspects 62-80, wherein hydrogen is added to the polymerization reactor system.

Aspect 83. The process defined in any one of aspects 62-82, wherein the olefin polymer has a density in any range disclosed herein, e.g., from about 0.87 to about 0.96, from about 0.87 to about 0.94, from about 0.88 to about 0.93, from about 0.89 to about 0.93, from about 0.93 to about 0.96, from about 0.90 to about 0.92 g/cm$^3$, etc.

Aspect 84. The process defined in any one of aspects 62-83, wherein the olefin polymer has a ratio of Mw/Mn in any range disclosed herein, e.g., from about 2 to about 18, from about 2.5 to about 15, from about 3 to about 15, from about 3 to about 12, etc.

Aspect 85. The process defined in any one of aspects 62-84, wherein the olefin polymer has a Mw in any range disclosed herein, e.g., from about 50,000 to about 750,000, from about 60,000 to about 600,000, from about 70,000 to about 500,000 g/mol, etc.

Aspect 86. The process defined in any one of aspects 62-85, wherein the olefin polymer has a Mn in any range disclosed herein, e.g., from about 10,000 to about 100,000, from about 12,000 to about 100,000, from about 14,000 to about 90,000 g/mol, etc.

Aspect 87. The process defined in any one of aspects 62-86, wherein the olefin polymer has a ratio of Mz/Mw in any range disclosed herein, e.g., from about 1.8 to about 10, from about 2 to about 9, from about 2 to about 8, etc.

Aspect 88. The process defined in any one of aspects 62-87, wherein the olefin polymer has a Mz in any range disclosed herein, e.g., from about 300,000 to about 1,500,000, from about 500,000 to about 1,500,000, from about 500,000 to about 1,000,000, from about 500,000 to about 1,000,000 g/mol, etc.

Aspect 89. The process defined in any one of aspects 62-88, wherein the olefin polymer has a HLMI in any range disclosed herein, e.g., less than about 200, less than about 100, less than about 50, less than about 25, from about 1 to about 200, from about 1 to about 100 g/10 min, etc.

Aspect 90. The process defined in any one of aspects 62-89, wherein the olefin polymer has a unimodal molecular weight distribution.

Aspect 91. An olefin polymer (e.g., an ethylene homopolymer or copolymer) produced by the olefin polymerization process defined in any one of aspects 62-90.

Aspect 92. An article comprising the olefin polymer defined in aspect 91.

Aspect 93. A method or forming or preparing an article of manufacture comprising an olefin polymer, the method comprising (i) performing the olefin polymerization process defined in any one of aspects 62-90 to produce an olefin polymer, and (ii) forming the article of manufacture comprising the olefin polymer, e.g., via any technique disclosed herein.

Aspect 94. The article defined in any one of aspects 92-93, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

We claim:

1. A method of making a bimetallic compound having the formula:

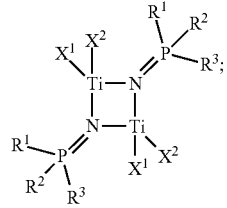

(A)

the method comprising:
contacting a half-metallocene titanium compound having the formula:

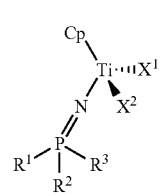

(B)

with an alkylaluminum compound having the formula $Al(R^Z)_3$ to form a mixture comprising the bimetallic compound having formula (A); wherein:
$X^1$ and $X^2$ independently are a halide;
$R^1$, $R^2$, and $R^3$ independently are H or a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group;
Cp is a substituted or unsubstituted cyclopentadienyl, indenyl, or fluorenyl group; and
each $R^Z$ independently is a $C_1$ to $C_{10}$ alkyl group.

2. The method of claim 1, wherein the alkylaluminum compound comprises trimethylaluminum, triethylaluminum, triisobutylaluminum, tri-n-octylaluminum, or any combination thereof.

3. The method of claim 1, wherein:
$X^1$ and $X^2$ are Cl;
$R^1$, $R^2$, and $R^3$ independently are H or $C_1$ to $C_{18}$ hydrocarbyl group; and
Cp is an unsubstituted cyclopentadienyl or indenyl group.

4. The method of claim 1, wherein each $R^Z$ independently is a $C_1$ to $C_8$ alkyl group.

5. The method of claim 1, wherein the mixture comprising the bimetallic compound is formed in a time period in a range from about 30 minutes to about 36 hours.

6. The method of claim 1, wherein the mixture comprising the bimetallic compound contains less than 10 wt. % of Ti(IV) compounds.

7. The method of claim 1, wherein:
the mixture further comprises Ti(II) compounds and/or additional Ti(III) compounds; and
the mixture contains less than 1 wt. % of Ti(IV) compounds.

8. The method of claim 1, wherein the molar ratio of the alkylaluminum compound to the half-metallocene titanium compound is in a range from about 1:1 to about 5:1.

9. The method of claim 1, wherein the molar ratio of the alkylaluminum compound to the half-metallocene titanium compound is in a range from about 1.1:1 to about 2:1.

10. A bimetallic titanium compound having the formula:

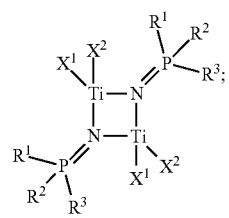

(A)

wherein:
$X^1$ and $X^2$ independently are a halide; and
$R^1$, $R^2$, and $R^3$ independently are H or a halide, $C_1$ to $C_{36}$ hydrocarbyl group, $C_1$ to $C_{36}$ halogenated hydrocarbyl group, $C_1$ to $C_{36}$ hydrocarboxy group, or $C_1$ to $C_{36}$ hydrocarbylsilyl group.

11. The compound of claim 10, wherein:
X$^1$ and X$^2$ are Cl; and
R$^1$, R$^2$, and R$^3$ independently are H or C$_1$ to C$_{18}$ hydrocarbyl group.

12. The compound of claim 10, wherein:
X$^1$ and X$^2$ are Cl; and
R$^1$, R$^2$, and R$^3$ independently are a C$_1$ to C$_8$ alkyl group.

13. A catalyst composition comprising a bimetallic titanium compound, an activator, and an optional co-catalyst, wherein the bimetallic titanium compound has the formula:

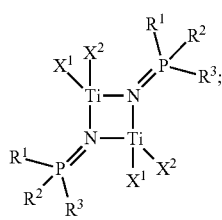
(A)

wherein:
X$^1$ and X$^2$ independently are a halide; and
R$^1$, R$^2$, and R$^3$ independently are H or a halide, C$_1$ to C$_{36}$ hydrocarbyl group, C$_1$ to C$_{36}$ halogenated hydrocarbyl group, C$_1$ to C$_{36}$ hydrocarboxy group, or C$_1$ to C$_{36}$ hydrocarbylsilyl group.

14. The composition of claim 13, wherein the activator comprises an aluminoxane compound, an organoboron or organoborate compound, an ionizing ionic compound, or any combination thereof.

15. The composition of claim 13, wherein the activator comprises an activator-support, the activator-support comprising a solid oxide treated with an electron-withdrawing anion.

16. The composition of claim 13, wherein:
the catalyst composition comprises an organoaluminum co-catalyst; and
the activator comprises a fluorided solid oxide and/or a sulfated solid oxide.

17. The composition of claim 13, wherein the catalyst composition is produced by a process comprising:
(a) contacting a half-metallocene titanium compound having the formula:

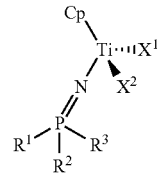
(B)

with an alkylaluminum compound having the formula Al(R$^Z$)$_3$ for a first period of time to form a first mixture, the first mixture comprising the bimetallic compound having formula (A); and
(b) contacting the first mixture with the activator and the co-catalyst for a second period of time to form the catalyst composition; wherein:
X$^1$ and X$^2$ independently are a halide;
R$^1$, R$^2$, and R$^3$ independently are H or a halide, C$_1$ to C$_{36}$ hydrocarbyl group, C$_1$ to C$_{36}$ halogenated hydrocarbyl group, C$_1$ to C$_{36}$ hydrocarboxy group, or C$_1$ to C$_{36}$ hydrocarbylsilyl group;
Cp is a substituted or unsubstituted cyclopentadienyl, indenyl, or fluorenyl group; and
each R$^Z$ independently is a C$_1$ to C$_{10}$ alkyl group.

18. An olefin polymerization process, the process comprising:
contacting the catalyst composition of claim 13 with an olefin monomer and an optional olefin comonomer in a polymerization reactor system under polymerization conditions to produce an olefin polymer.

19. The process of claim 18, wherein:
the polymerization reactor system comprises a slurry reactor, gas-phase reactor, solution reactor, or a combination thereof; and
the olefin monomer comprises ethylene, and the olefin comonomer comprises 1-butene, 1-hexene, 1-octene, or a mixture thereof.

20. The process of claim 18, wherein:
the olefin polymer comprises an ethylene homopolymer or an ethylene/α-olefin copolymer;
the activator comprises an activator-support, an aluminoxane compound, an organoboron or organoborate compound, an ionizing ionic compound, or any combination thereof; and
the catalyst composition comprises an organoaluminum co-catalyst.

* * * * *